United States Patent
Lawson et al.

(10) Patent No.: US 12,240,797 B2
(45) Date of Patent: Mar. 4, 2025

(54) METHOD OF PREPARING A DON PRODRUG FROM L-GLUTAMIC ACID

(71) Applicants: DRACEN PHARMACEUTICALS, INC., Washington, DC (US); Pavel Majer, Sykesville, MD (US); Ivan Šnajdr, Prague (CZ); Martin Hadzima, Kosice (SK); Lukáš Tenora, Kretín (CZ); Jon Philip Lawson, Wildwood, MO (US); Robert Christian Wild, Murrieta, CA (US); Yiyang Shao, Beijing (CN); Jinxiao Chu, Beijing (CN); Jinchao Weng, Beijing (CN)

(72) Inventors: Jon Philip Lawson, Wildwood, MO (US); Robert Christian Wild, Murrieta, CA (US); Yiyang Shao, Beijing (CN); Jinchao Weng, Beijing (CN); Pavel Majer, Sykesville, MD (US); Ivan Šnajdr, Prague (CZ); Martin Hadzima, Kosice (SK); Lukáš Tenora, Kretín (CZ); Jinxiao Chu, Beijing (CN)

(73) Assignee: DRACEN PHARMACEUTICALS, INC., Washington, DC (US)

( * ) Notice: Subject to any disclaimer, the term of this patent is extended or adjusted under 35 U.S.C. 154(b) by 780 days.

(21) Appl. No.: 17/430,286

(22) PCT Filed: Feb. 11, 2020

(86) PCT No.: PCT/US2020/017750
§ 371 (c)(1),
(2) Date: Aug. 11, 2021

(87) PCT Pub. No.: WO2020/167831
PCT Pub. Date: Aug. 20, 2020

(65) Prior Publication Data
US 2022/0089522 A1 Mar. 24, 2022

(30) Foreign Application Priority Data

Feb. 11, 2019 (WO) ............... PCT/CN2019/074802

(51) Int. Cl.
*C07C 249/02* (2006.01)
*C07D 209/18* (2006.01)
*C07D 209/20* (2006.01)

(52) U.S. Cl.
CPC ................. *C07C 249/02* (2013.01)

(58) Field of Classification Search
CPC .... C07C 249/02; C07D 209/18; C07D 209/20
See application file for complete search history.

(56) References Cited

U.S. PATENT DOCUMENTS

| | | |
|---|---|---|
| 10,336,778 B2 | 7/2019 | Slusher et al. |
| 10,568,868 B2 | 2/2020 | Slusher et al. |
| 10,738,066 B2 | 8/2020 | Slusher et al. |
| 10,799,605 B2 | 10/2020 | Osterkamp et al. |
| 10,842,763 B2 | 11/2020 | Slusher et al. |
| 10,954,257 B2 | 3/2021 | Slusher et al. |
| 2018/0221337 A1 | 8/2018 | Slusher et al. |
| 2018/0221395 A1 | 8/2018 | Slusher et al. |
| 2018/0222930 A1 | 8/2018 | Slusher et al. |
| 2019/0315783 A1 | 10/2019 | Slusher et al. |
| 2019/0315784 A1 | 10/2019 | Slusher et al. |
| 2022/0194898 A1 | 6/2022 | Lawson et al. |

FOREIGN PATENT DOCUMENTS

| | | |
|---|---|---|
| JP | 2005272404 A | 10/2005 |
| JP | 2017519001 A | 7/2017 |
| WO | WO-2004113363 A1 | 12/2004 |
| WO | WO-2017023774 A1 | 2/2017 |
| WO | WO-2017023787 A1 | 2/2017 |
| WO | WO-2017023791 A1 | 2/2017 |
| WO | WO-2017023793 A2 | 2/2017 |

(Continued)

OTHER PUBLICATIONS

Abo-Ghalia, M., et al., "Synthesis of inhibitors of the meso-diaminopimelate—adding enzyme from *Escherichia coli*," Int J Pept Protein Res 32(3):208-22, Wiley, United States (Sep. 1988).
Pettit, G.R., et al., "Synthesis of azotomycin," J. Org. Chem. 51(8):1282-1286, American Chemical Society, United States (Apr. 1986).
Montalbetti, C., et al., "Amine bond formation and peptide coupling," Tetrahedron 61:10827-10852, Elsevier, Netherlands (Aug. 2005).
Ahluwalia, G.S., et al., "Metabolism and action of amino acid analog anti-cancer agents," Pharmacology and Therapeutics 46(2):243-271, Elsevier (1990).

(Continued)

*Primary Examiner* — Laura L Stockton
(74) *Attorney, Agent, or Firm* — Sterne, Kessler, Goldstein & Fox P.L.L.C.

(57) ABSTRACT

The present disclosure provides methods of preparing a compound of Formula (I): wherein $R^1$, $R^2$, and $R^3$ are as defined as set forth in the application. In one embodiment, a compound of Formula (I) is prepared in >95% chemical purity and >95% enantiomeric excess.

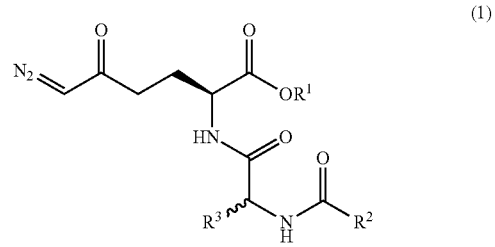

(I)

20 Claims, 4 Drawing Sheets

(56) References Cited

FOREIGN PATENT DOCUMENTS

| WO | WO-2019071110 A1 | 4/2019 |
| WO | WO-2020167829 A1 | 8/2020 |

OTHER PUBLICATIONS

Bitta, J., and Kubik, S., "Cyclic hexapeptides with free carboxylate groups as new receptors for monosaccharides," *Organic Letters* 3(17):2637-2640, American Chemical Society (2001).

Hobbs, M.J., et al., "Elevation of Endogenous Nucleophiles in Rat Lung by Cysteine and Glutathione Esters *In Vitro*," *Biochemical Pharmacology* 55:1573-1584, Elsevier (1998).

International Search Report and Written Opinion for International Application No. PCT/US2020/017750, Commissioner for Patents, United States, mailed on Apr. 29, 2020, 7 pages.

Lynch, G., et al., "Phase II evaluation of DON (6-diazo-5-oxo-L-norleucine) in patients with advanced colorectal carcinoma," *American Journal of Clinical Oncology* 5(5):541-543, Lippincott Williams & Wilkins (1982).

Moss, G.P., "Basic Terminology of Stereochemistry," *Pure& Appl. Chem.* 68:2193-2222, International Union of Pure and Applied Chemistry, Walter de Gruyter (1996).

Rosenfeld, H., and Roberts, J., "Enhancement of Antitumor Activity of Glutamine Antagonists 6-Diazo-5-oxo-L-norleucine and Acivicin in Cell Culture by Glutaminase-Asparaginase," *Cancer Research* 41:1324-1328, American Association for Cancer Research (1981).

METHOD OF PREPARING A DON PRODRUG FROM L-GLUTAMIC ACID

BACKGROUND OF THE INVENTION

6-Diazo-5-oxo-L-norleucine (DON) is a glutamine antagonist that exhibits promising activity in preclinical models to treat a variety of diseases such as cancer. See, e.g., Ahluwalia et al., *Pharmac The.* 46:243-371 (1990). But the clinical development of DON has been hampered by its dose-limiting toxicity in humans, especially in the intestinal epithelium. See, e.g., Rosenfeld and Roberts, *Cancer Research* 41:1324-1328 (1981) and Lynch et al., *Am J Clin Oncol* (*CCT*) 5:541-543 (1982). Administering DON as a prodrug may help mitigate this toxicity.

WO 2017/023774 discloses isopropyl (S)-2-((S)-2-acetamido-3-(1H-indol-3-yl)propanamido)-6-diazo-5-oxohexanoate and other prodrugs of DON, and methods to make these prodrugs. DON prodrugs can be used to treat cancer, cognitive deficits, metabolic reprogramming disorders, and other diseases. See WO 2017/023793, WO 2017/023791, and WO 2017/023787.

There exists a need for improved methods to prepare DON prodrugs. Alkyl esters of (S)-2-amino-6-diazo-5-oxohexanoate, for example, isopropyl (S)-2-amino-6-diazo-5-oxohexanoate and ethyl (S)-2-amino-6-diazo-5-oxohexanoate, are putative synthetic intermediates that can be used in this process. But these compounds may cyclize under mild conditions to give undesired cyclized products. In particular, isopropyl (S)-2-amino-6-diazo-5-oxohexanoate and ethyl (S)-2-amino-6-diazo-5-oxohexanoate cyclize to give isopropyl (S)-5-(diazomethyl)-3,4-dihydro-2H-pyrrole-2-carboxylate and ethyl (S)-5-(diazomethyl)-3,4-dihydro-2H-pyrrole-2-carboxylate, respectfully. See WO 2017/023774. The chemical instability of isopropyl (S)-2-amino-6-diazo-5-oxohexanoate, ethyl (S)-2-amino-6-diazo-5-oxohexanoate, and other alkyl esters of (S)-2-amino-6-diazo-5-oxohexanoate limits their usefulness as synthetic intermediates, especially in large-scale syntheses that may require reaction conditions that are incompatible with their propensity to cyclize and/or decompose by other mechanisms.

BRIEF SUMMARY OF THE INVENTION

Applicant has unexpectedly found a reaction pathway for the synthesis of DON prodrugs using intermediates which can be easily and effectively purified by introducing the diazo-group at a late stage of the reaction, thereby preventing the cyclization and decomposition of less stable intermediates. In particular, applicant has unexepectedly found that isopropyl (S)-2-((S)-2-acetamido-3-(1H-indol-3-yl)propanamido)-6-diazo-5-oxohexanoate can be obtained in high chemical purity and in high enantiomeric excess by reacting (S)-4-((S)-2-acetamido-3-(1H-indol-3-yl)propanamido)-5-isopropoxy-5-oxopentanoic (ethyl carbonic) anhydride with diazomethane in a solvent.

In one aspect, the disclosure provides a method of preparing a compound of Formula (1):

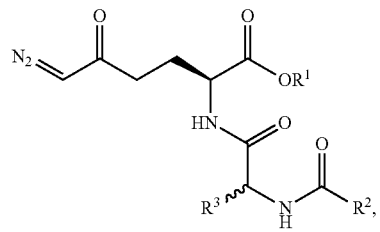

wherein:
R$^1$ is selected from the group consisting of C$_1$-C$_8$ alkyl (linear or branched, wherein branched alkyls are preferred), C$_6$-C$_{10}$ aryl, C$_6$-C$_{10}$-aryl-C$_1$-C$_3$-alkyl, and C$_3$-C$_{10}$ cycloalkyl;

R$^3$ is an amino acid side chain; or

R$^3$ is selected from the group consisting of C$_1$-C$_6$ alkyl, (aryl)alkyl, and (heteroaryl)alkyl;

R$^2$ is selected from the group consisting of C$_1$-C$_8$ alkyl, C$_6$-C$_{10}$ aryl, C$_6$-C$_{10}$-aryl-C$_1$-C$_3$-alkyl, C$_3$-C$_{10}$ cycloalkyl, C$_3$-C$_{10}$ heterocycloalkyl containing at least one heteroatom selected from the group consisting of N, S, and O, 5- to 9-membered heteroaryl containing at least one heteroatom selected from the group consisting of N, S, and O, and C$_3$-C$_8$ heterocycloalkyl containing at least one heteroatom selected from the group consisting of N, S, and O, wherein each of the substituent groups may optionally be substituted; or R$^2$ is R$^5$;

R$^5$ is —X—R$^{5'}$;

—X— is —O— or —NH—; and

R$^{5'}$ is selected from the group consisting of C$_1$-C$_8$ alkyl, C$_6$-C$_{10}$ aryl, C$_6$-C$_{10}$-aryl-C$_1$-C$_3$-alkyl, C$_3$-C$_{10}$ cycloalkyl, C$_3$-C$_{10}$ heterocycloalkyl containing at least one heteroatom selected from the group consisting of N, S, and O, 5- to 9-membered heteroaryl containing at least one heteroatom selected from the group consisting of N, S, and O, and C$_3$-C$_8$ heterocycloalkyl containing at least one heteroatom selected from the group consisting of N, S, and O, wherein each of the substituent groups may optionally be substituted;

said method comprising reacting a compound of Formula (6):

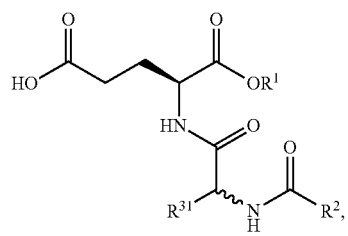

wherein R$^1$ and R$^2$ are as defined above, and

R$^{31}$ is R$^3$ or a precursor of R$^3$.

with a branched C$_3$-C$_8$-alkyl chloroformate or C$_4$-C$_8$-cycloalkyl chloroformate and diazomethane in basic conditions to yield the compound of Formula (1).

In another aspect, the disclosure provides a method of preparing a compound of Formula I:

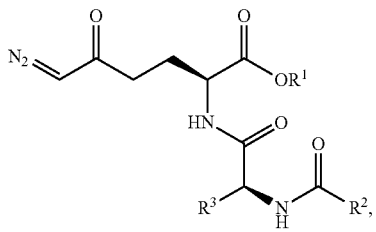

(I)

wherein $R^1$ is $C_1$-$C_4$ alkyl; $R^2$ is $C_1$-$C_4$ alkyl; and $R^3$ is selected from the group consisting of $C_1$-$C_6$ alkyl, (aryl)alkyl, and (heteroaryl)alkyl.

In another aspect, the disclosure provides a method of preparing a compound of Formula (1) or Formula I in >95% chemical purity and/or >95% enantiomeric excess.

In another aspect, the disclosure provides a method of preparing isopropyl (S)-2-((S)-2-acetamido-3-(1H-indol-3-yl)propanamido)-6-diazo-5-oxohexanoate in >95% chemical purity and >95% enantiomeric excess.

DETAILED DESCRIPTION OF THE INVENTION

Figure 1:
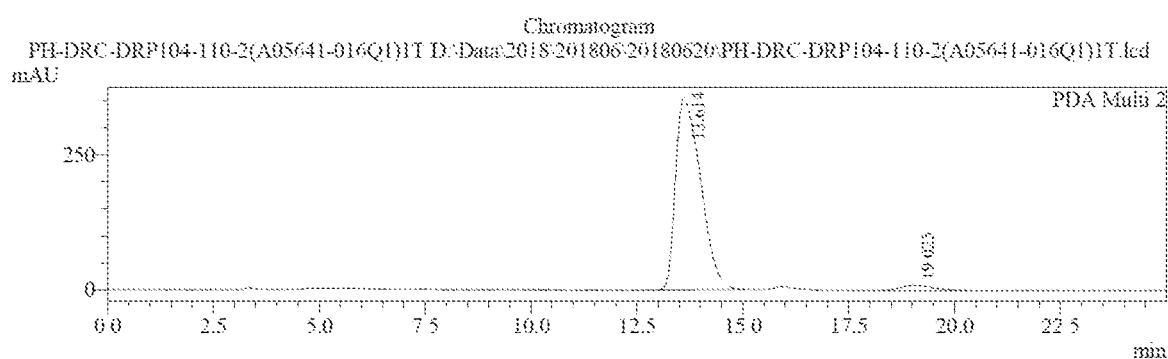
FIG. 1 is a chiral HPLC chromatogram showing enantiomeric excess (ee) of Compound A1.

In one embodiment (referred as "Embodiment I"), the disclosure provides a method of preparing a compound of Formula (1):

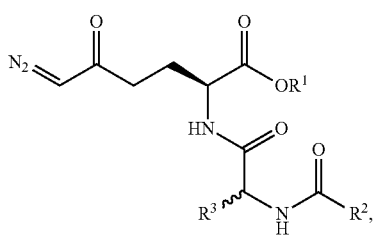

(1)

wherein:
$R^1$ is selected from the group consisting of $C_1$-$C_8$ alkyl (linear or branched, wherein branched alkyls are preferred), $C_6$-$C_{10}$ aryl, $C_6$-$C_{10}$-aryl-$C_1$-$C_3$-alkyl and $C_3$-$C_{10}$ cycloalkyl;

$R^3$ is an amino acid side chain;

$R^2$ is selected from the group consisting of $C_1$-$C_8$ alkyl, $C_6$-$C_{10}$ aryl, $C_6$-$C_{10}$-aryl-$C_1$-$C_3$-alkyl, $C_3$-$C_{10}$ cycloalkyl, $C_3$-$C_{10}$ heterocycloalkyl containing at least one heteroatom selected from the group consisting of N, S, and O, 5- to 9-membered heteroaryl, and $C_3$-$C_8$ heterocycloalkyl containing at least one heteroatom selected from the group consisting of N, S, and O, wherein each of the substituent groups may optionally be substituted;

or $R^2$ is $R^5$;

$R^5$ is —X—$R^{5'}$, wherein —X— is —O— or —NH— and $R^{5'}$ is selected from the group consisting of $C_1$-$C_8$ alkyl, $C_6$-$C_{10}$ aryl, $C_6$-$C_{10}$-aryl-$C_1$-$C_3$-alkyl, $C_3$-$C_{10}$ cycloalkyl, $C_3$-$C_{10}$ heterocycloalkyl containing at least one heteroatom selected from the group consisting of N, S, and O, 5- to 9-membered heteroaryl, and $C_3$-$C_8$ heterocycloalkyl containing at least one heteroatom selected from the group consisting of N, S, and O, wherein each of the substituent groups may optionally be substituted;

the method comprising reacting a compound of Formula (6):

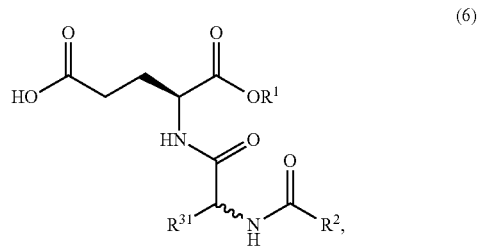

(6)

wherein $R^1$ and $R^2$ are as defined above, and $R^{31}$ is $R^3$ or a precursor of $R^3$, with a branched $C_3$-$C_8$-alkyl chloroformate or $C_4$-$C_8$-cycloalkyl chloroformate and diazomethane in basic conditions to yield the compound of Formula (1).

In another embodiment in connection with the preparation of Formula (1), $R^1$ is isopropyl.

In another embodiment in connection with the preparation of Formula (1), the side chains of tryptophan (in particular L-tryptophan) and leucine are most preferred substituents $R^3$.

In another embodiment in connection with the preparation of Formula (1), the reaction of a compound of Formula (6) to form a compound of Formula (1) may preferably be carried out in ethers, esters, chlorinated solvents or mixtures thereof, more preferably in a solvent selected from the group consisting of tetrahydrofuran, ethyl acetate, diethylether, dichloromethane, and chloroform.

In another embodiment in connection with the preparation of Formula (1), the reaction of a compound of Formula (6) to form a compound of Formula (1) may preferably be carried in the presence of a base, preferably tertiary amine base such as triethylamine or N,N-diisopropylethylamine.

In another embodiment in connection with the preparation of Formula (1), the compound of Formula (6) is prepared by hydrogenating a compound of Formula (5):

(5)

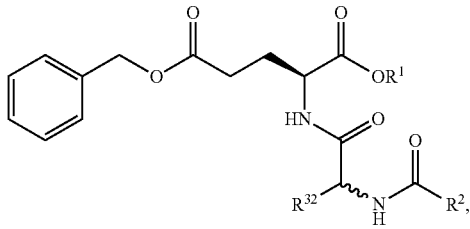

wherein
$R^{32}$ is $R^3$ or a precursor of $R^3$; and
$R^2$ together with the carbonyl group to which it is bound forms a protecting group; or
$R^2$ is $R^5$.

In another embodiment in connection with the preparation of Formula (1), the protecting group formed by $R^2$ together with the carbonyl group to which it is bound is a protecting group for protecting amino groups. Such groups typically include 9-fluorenylmethyloxycarbonyl (FMOC), t-butyloxycarbonyl (BOC), acetyl (Ac), and trifluoroacetyl. In another embodiment, the protecting group formed by $R^2$ together with the carbonyl group to which it is bound is benzyloxycarbonyl, i.e., $R^2$ is benzyloxy.

In another embodiment in connection with the preparation of Formula (1), hydrogenation of compound of Formula (5) may be preferably carried out with $H_2$ on Pd/C, more preferably in a solvent selected from ethers, esters, chlorinated solvents or mixtures thereof, in particular selected from tetrahydrofuran, ethyl acetate, or diethylether.

In another embodiment in connection with the preparation of Formula (1), the compound of Formula (5) is prepared by:
a) reacting a compound of Formula (2):

(2)

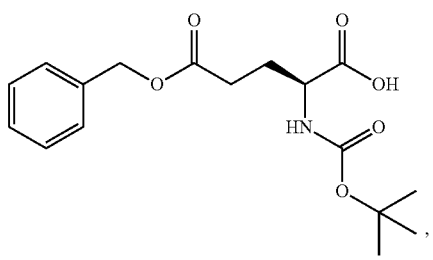

with $R^1$—$X^1$, wherein $X^1$ is a halogen, to yield a compound of Formula (3):

(3)

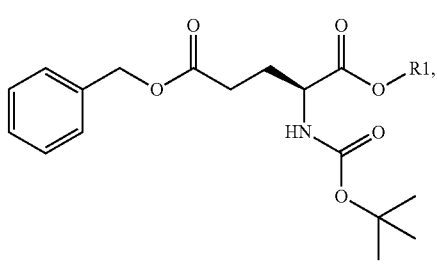

b) reacting the compound of Formula (3) with trifluoroacetic acid to yield a compound of Formula (4):

(4)

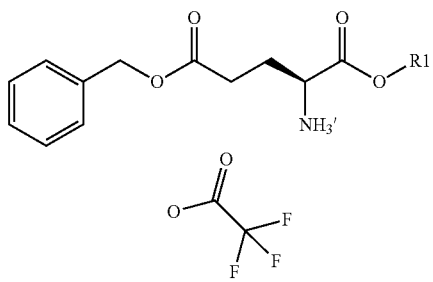

c) converting the compound of Formula (4) by reaction with an amino acid or a protected amino acid to a compound of Formula (5):

(5)

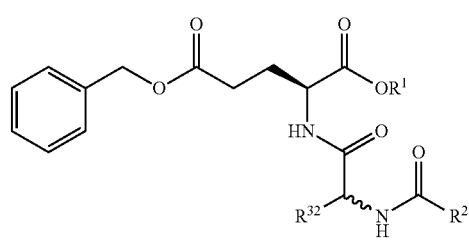

optionally followed by:
c1) replacing $R^2$ by another $R^2$ or by $R^3$ (i.e., replacing one protecting group by another protecting group or by $R^5$).

Step a) may be carried out in an ether solvent such as tetrahydrofuran (THF) and in the presence of a base such as tetrabutylammonium iodide (TBAI) and 1,8-diazabicyclo[5.4.0]undec-7-ene (DBU).

$R^1$—$X^1$ in step a) is most preferably 2-bromopropane.

Step b) is preferably performed in a chlorinated solvent such as dichloromethane.

Step c) is preferably performed in a chlorinated solvent such as dichloromethane in the presence of a peptide coupling reagent such as HATU (hexafluorophosphate azabenzotriazole tetramethyl uronium) and in the presence of a base such as N,N-diisopropylethylamine (DIEA) or triethylamine.

The disclosure also provides the following particular embodiments with respect to the preparation of a compound of Formula (1).

Embodiment II

The method according to Embodiment I, wherein the reaction of a compound of Formula (6) to form a compound of Formula (1) is carried out in ethers, esters, chlorinated solvents or mixtures thereof, more preferably in a solvent selected from the group consisting of tetrahydrofuran, ethyl acetate, diethylether, dichloromethane, and chloroform.

Embodiment III

The method according to Embodiments I or II, wherein the reaction of a compound of Formula (6) to form a compound of Formula (1) is carried out in the presence of a base, preferably a tertiary amine base.

Embodiment IV

The method according to any one of Embodiments I-IV, wherein the compound of Formula (6) is prepared by hydrogenating a compound of Formula (5):

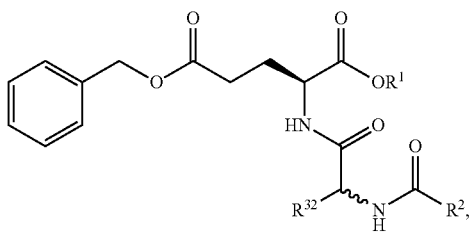

(5)

wherein $R^{32}$ is $R^3$ or a precursor of $R^3$; and $R^2$ together with the carbonyl group to which it is bound forms a protecting group; or $R^2$ is $R^5$.

Embodiment V

The method according to Embodiment IV, wherein $R^2$ is selected from the group consisting of 9-fluorenylmethyloxy, t-butyloxy, methyl, trifluoromethyl, and benzyloxy.

Embodiment VI

The method according to Embodiments IV or V, wherein the hydrogenation of the compound of Formula (5) is carried out with $H_2$ on Pd/C, preferably in a solvent selected from ethers, esters, chlorinated solvents or mixtures thereof.

Embodiment VII

The method according to any one of Embodiments IV to VI, wherein the compound of Formula (5) is prepared by:

a) reacting a compound of Formula (2):

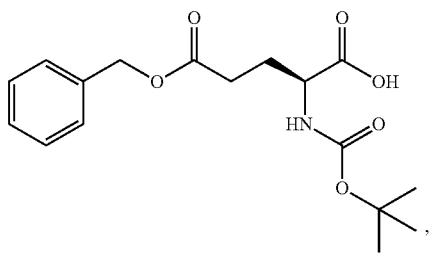

(2)

with $R^1$—$X^1$, wherein $X^1$ is a halogen, to yield a compound of Formula (3):

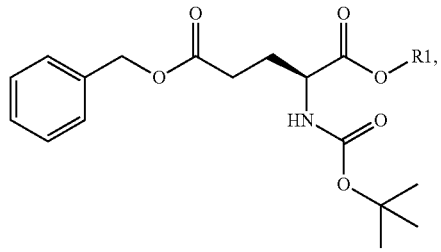

(3)

b) reacting the compound of Formula (3) with trifluoroacetic acid to yield a compound of Formula (4):

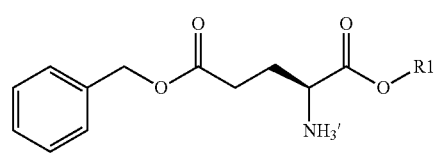

(4)

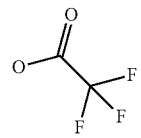

c) converting the compound of Formula (4) by reaction with an amino acid or a protected amino acid to a compound of Formula (5):

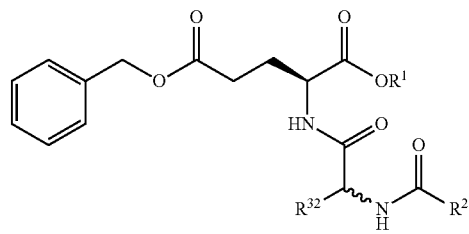

(5)

optionally followed by:

c1) replacing $R^2$ by another $R^2$ or by $R^5$.

Embodiment VIII

The method according to Embodiment I, wherein the compound of Formula (1) is isopropyl (S)-2-((S)-acetamido-3-(1H-indol-3-yl)propanamido)-6-diazo-5-oxohexanoate (Compound 1a), and the method includes the following reaction sequence:

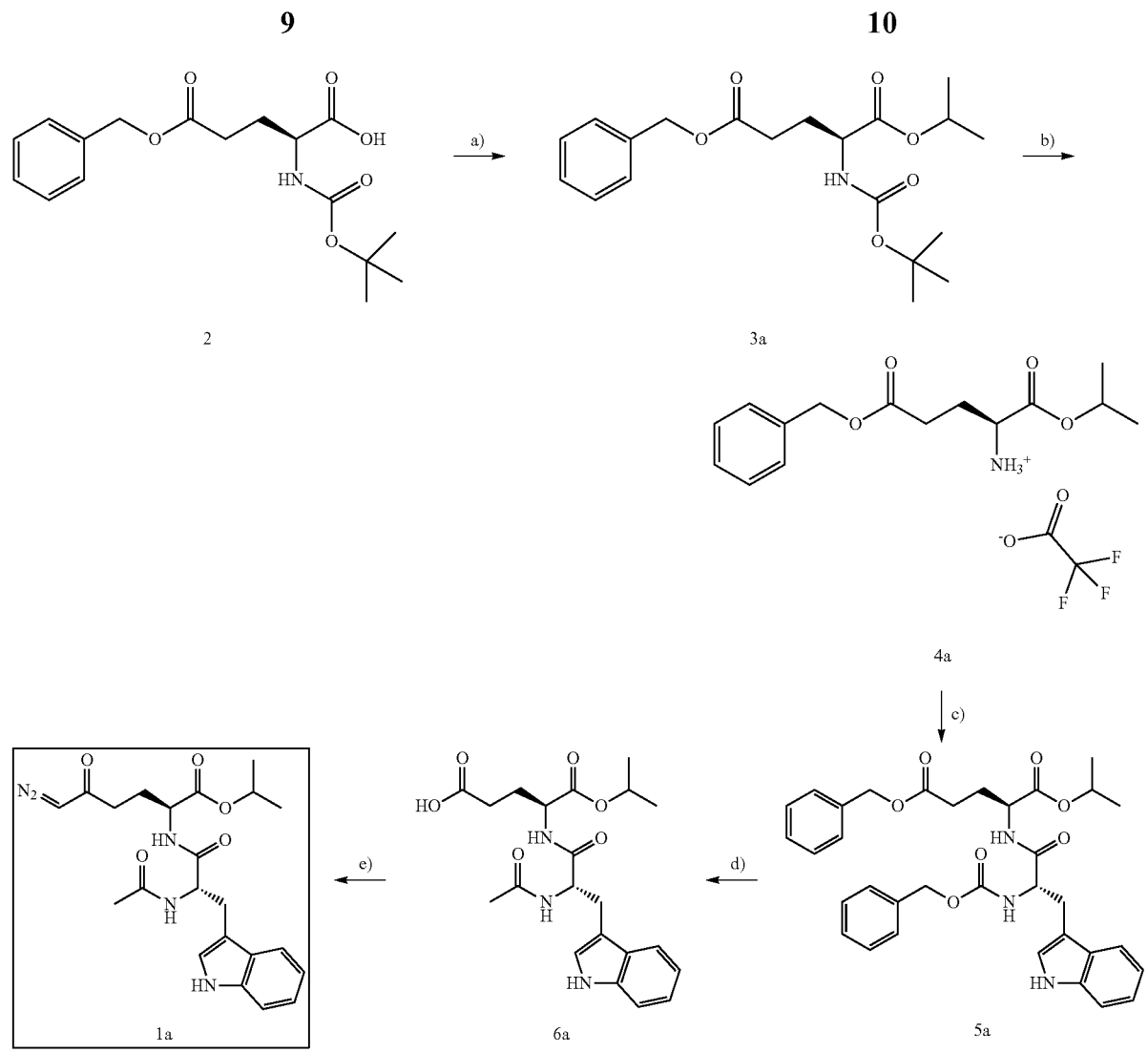
Embodiment IX
The method according to Embodiment I, wherein the compound of Formula (1) is isopropyl (S)-2-((S)-acetamido-3-(1H-indol-3-yl) propanamido)-6-diazo-5-oxohexanoate (Compound 1a), and the method includes the following reaction sequence:
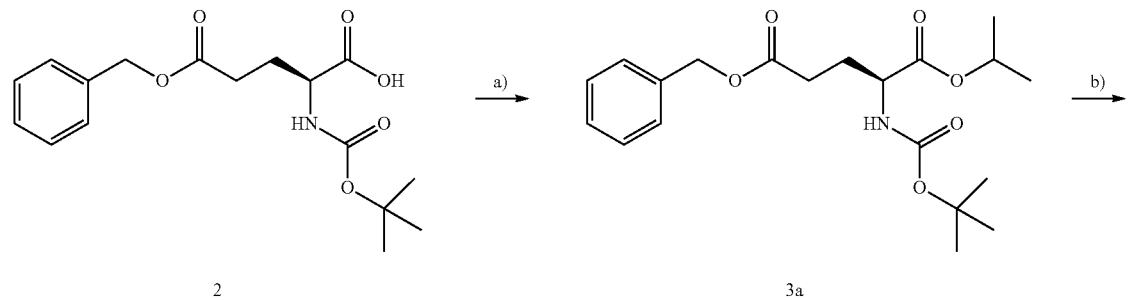

-continued
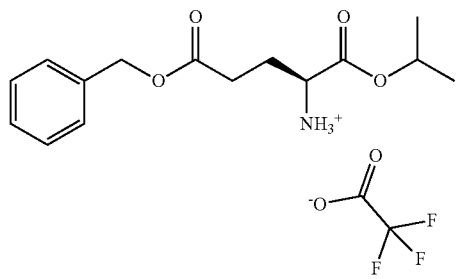
4a
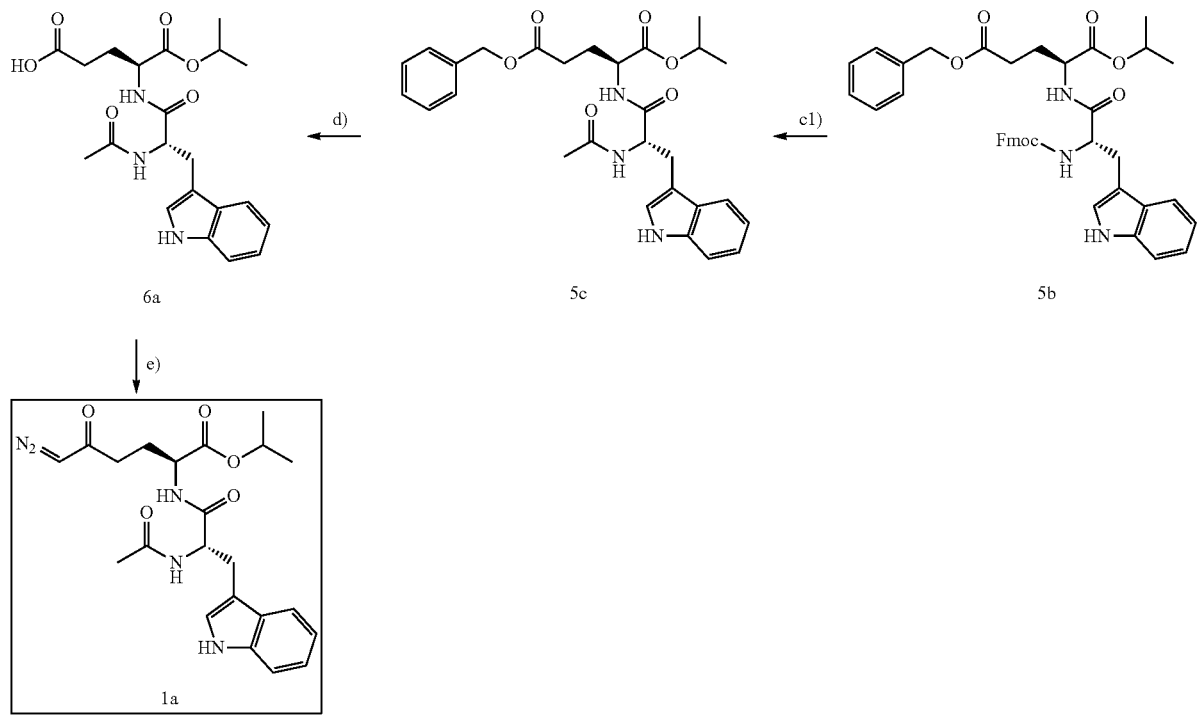
6a    5c    5b
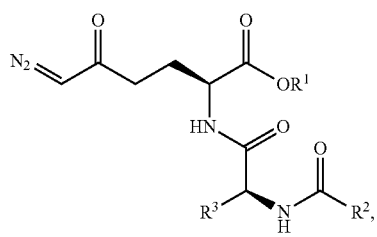
1a
In another embodiment, the disclosure provides a method of preparing a compound of Formula I:
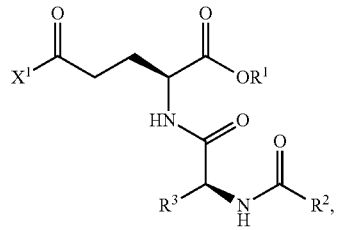
I
the method comprising:
(a) reacting a compound of Formula II:
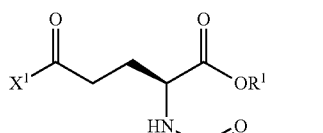
II
with diazomethane in a solvent at a temperature of about −78° C. to about 0° C., wherein:
$X^1$ is selected from the group consisting of halogen, benzotriazole,

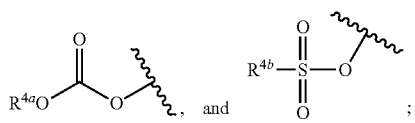

$R^1$ is $C_1$-$C_4$ alkyl;
$R^2$ is $C_1$-$C_4$ alkyl;
$R^3$ is selected from the group consisting of $C_1$-$C_6$ alkyl, (aryl)alkyl, and (heteroaryl)alkyl;
$R^{4a}$ is selected from the group consisting of $C_1$-$C_8$ alkyl and $C_3$-$C_8$ cycloalkyl; and
$R^{4b}$ is selected from the group consisting of $C_1$-$C_8$ alkyl and —$CF_3$.

In another embodiment, the disclosure provides a method of preparing a compound of Formula I further comprising (b) isolating the compound of Formula I.

In another embodiment in connection with the preparation of the compound of Formula I, $X^1$ is

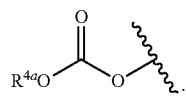

In another embodiment in connection with the preparation of the compound of Formula I, the solvent is selected from the group consisting of tetrahydrofuran, 2-methyltetrahydrofuran, diethyl ether, and N,N-dimethylformamide. In another embodiment, the solvent is selected from the group consisting of tetrahydrofuran and diethyl ether, or a combination thereof.

In another embodiment in connection with the preparation of the compound of Formula I, the temperature is about −45° C. to about −10° C.

In another embodiment in connection with the preparation of the compound of Formula I, wherein the compound of Formula II is prepared in situ and reacted with diazomethane without isolation or purification.

In another embodiment in connection with the preparation of the compound of Formula I, the stereomutation of a compound of Formula II is less than about 2%. In another embodiment, the stereomutation of a compound having Formula II is less than about 1%.

In another embodiment in connection with the preparation of the compound of Formula I, the compound of Formula I is obtained in about 95% ee or more (as determined by chiral HPLC). In another embodiment, the compound of Formula I is obtained in about 96% ee or more. In another embodiment, the compound of Formula I is obtained in about 97% ee or more. In another embodiment, the compound of Formula I is obtained in about 98% ee or more. In another embodiment, the compound of Formula I is obtained in about 99% ee or more.

In another embodiment in connection with the preparation of the compound of Formula I, the compound of Formula I is obtained in a chemical purity (as determined by HPLC) of about 95% or more. In another embodiment, the compound of Formula I is obtained in a chemical purity of about 96% or more. In another embodiment, the compound of Formula I is obtained in a chemical purity of about 97% or more. In another embodiment, the compound of Formula I is obtained in a chemical purity of about 98% or more. In another embodiment, the compound of Formula I is obtained in a chemical purity of about 99% or more.

In another embodiment in connection with the preparation of the compound of Formula I, the compound of Formula I is obtained in a chemical yield of about 50% or more. In another embodiment, the compound of Formula I is obtained in a chemical yield of about 55% or more. In another embodiment, the compound of Formula I is obtained in a chemical yield of about 60% or more. In another embodiment, the compound of Formula I is obtained in a chemical yield of about 65% or more. In another embodiment, the compound of Formula I is obtained in a chemical yield of about 70% or more. In another embodiment, the compound of Formula I is obtained in a chemical yield of about 75% or more. In another embodiment, the compound of Formula I is obtained in a chemical yield of about 80% or more. In another embodiment, the compound of Formula I is obtained in a chemical yield of about 85% or more. In another embodiment, the compound of Formula I is obtained in a chemical yield of about 90% or more. In another embodiment, the compound of Formula I is obtained in a chemical yield of about 95% or more.

In another embodiment in connection with the preparation of the compound of Formula I, the compound of Formula II, e.g., (S)-4-((S)-2-acetamido-3-(1H-indol-3-yl)propanamido)-5-isopropoxy-5-oxopentanoic (ethyl carbonic) anhydride, is used as a starting material in an amount of 100 g or more. In another embodiment, Formula II is used as a starting material in an amount of 250 g or more. In another embodiment, Formula II is used as a starting material in an amount of 500 g or more. In another embodiment, Formula II is used as a starting material in an amount of 1000 g or more.

In another embodiment, the disclosure provides a method of preparing a compound of Formula II:

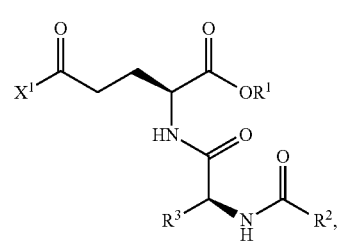

wherein:
$X^1$ is:

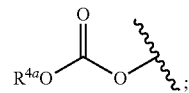

and
$R^{4a}$ is selected from the group consisting of $C_1$-$C_8$ alkyl and $C_3$-$C_8$ cycloalkyl;
the method comprising reacting a compound of Formula III:

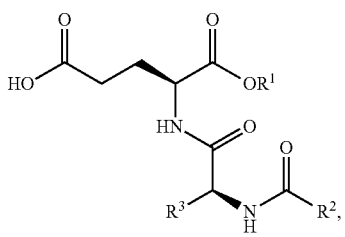

wherein:
R¹ is $C_1$-$C_4$ alkyl;
R² is $C_1$-$C_4$ alkyl; and
R³ is selected from the group consisting of $C_1$-$C_6$ alkyl, (aryl)alkyl, and (heteroaryl)alkyl;
with a compound having Formula IV:

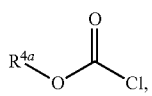

wherein $R^{4a}$ is selected from the group consisting of $C_1$-$C_8$ alkyl and $C_3$-$C_8$ cycloalkyl, in a solvent in the presence of a base at a temperature of about −45° C. to about 20° C.

In another embodiment, in connection with the preparation of a compound of Formula II, $R^{4a}$ is methyl.

In another embodiment, in connection with the preparation of a compound of Formula II, $R^{4a}$ is ethyl.

In another embodiment, in connection with the preparation of a compound of Formula II, the solvent is selected from the group consisting of tetrahydrofuran, 2-methyltetrahydrofuran, and diethyl ether, or a combination thereof.

In another embodiment, in connection with the preparation of a compound of Formula II, the temperature is about −30° C. to about −10° C. In one embodiment, the temperature is −25° C.

In another embodiment, in connection with the preparation of a compound of Formula II, the reaction is in the presence of a base. In another embodiment, the base is selected from a group of triethylamine and N,N-diisopropylethylamine. In one embodiment, the base is triethylamine.

In another embodiment, the disclosure provides a method of preparing a compound of Formula III:

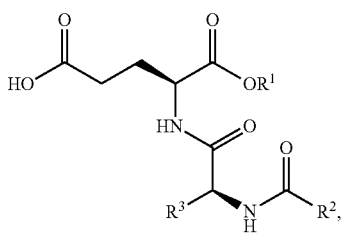

the method comprising reacting a compound of Formula V:

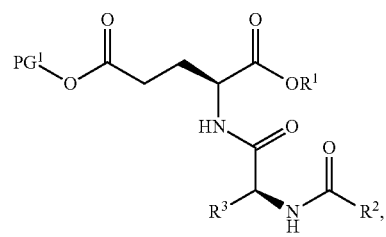

wherein:
R¹ is $C_1$-$C_4$ alkyl;
R² is $C_1$-$C_4$ alkyl;
R³ is selected from the group consisting of $C_1$-$C_6$ alkyl, (aryl)alkyl, and (heteroaryl)alkyl; and
$PG^1$ is a protecting group,
with a deprotecting agent in a solvent at a temperature of about 0° C. to about 60° C.

In another embodiment in connection with the preparation of a compound of Formula III, the $PG^1$ is $C_1$-$C_6$ alkyl, and the deprotecting agent is an acid. In one embodiment, the acid is selected from the group consisting of trifluoroacetic acid and hydrochloric acid.

In another embodiment in connection with the preparation of a compound of Formula III, the solvent is selected from the group consisting of dichloromethane, chloroform, tetrahydrofuran, and 2-methyltetrahydrofuran. In one embodiment, the solvent is dichloromethane.

In another embodiment in connection with the preparation of a compound of Formula III, the temperature is about 15° C. to about 30° C. In one embodiment, the temperature is 25° C.

In another embodiment in connection with the preparation of the compound of Formula III, the stereomutation of a compound of Formula V is less than about 6%. In another embodiment, the stereomutation of a compound having Formula V is less than about 5%, about 4%, about 3%, about 2%, about 1%, or about 0.1%.

In another embodiment in connection with the preparation of the compound of Formula III, the compound of Formula III is obtained in about 95% ee or more (as determined by chiral HPLC). In another embodiment, the compound of Formula III is obtained in about 96% ee or more. In another embodiment, the compound of Formula III is obtained in about 97% ee or more. In another embodiment, the compound of Formula III is obtained in about 98% ee or more. In another embodiment, the compound of Formula III is obtained in about 99% ee or more.

In another embodiment in connection with the preparation of the compound of Formula III, the compound of Formula III is obtained in a chemical purity (as determined by HPLC) of about 95% or more. In another embodiment, the compound of Formula III is obtained in a chemical purity of about 96% or more. In another embodiment, the compound of Formula III is obtained in a chemical purity of about 97% or more. In another embodiment, the compound of Formula III is obtained in a chemical purity of about 98% or more. In another embodiment, the compound of Formula III is obtained in a chemical purity of about 99% or more.

In another embodiment in connection with the preparation of a compound of Formula III, $PG^1$ is aralkyl, and the deprotecting agent is hydrogen in the presence of a catalyst. In one embodiment, the catalyst is palladium on carbon. In another embodiment, the solvent is selected from the group consisting of tetrahydrofuran, 2-methyltetrahydrofuran, methanol, and ethyl acetate. In another embodiment, the temperature is about 15° C. to about 30° C.

In another embodiment, the disclosure provides a method of preparing a compound of Formula V:

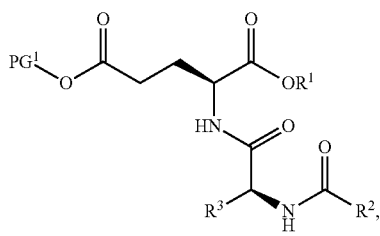

the method comprising reacting a compound of Formula VI:

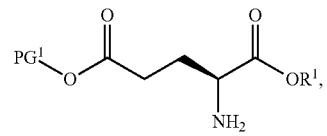

wherein:
$R^1$ is $C_1$-$C_4$ alkyl; and
$PG^1$ is a protecting group,
with a compound of Formula VII:

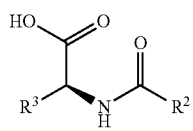

wherein:
$R^2$ is $C_1$-$C_4$ alkyl; and
$R^3$ is selected from the group consisting of $C_1$-$C_6$ alkyl, (aryl)alkyl, and (heteroaryl)alkyl;
in a solvent in the presence of a coupling agent at a temperature of about 0° C. to about 60° C.

In another embodiment in connection with the preparation of a compound of Formula V, the coupling agent comprises a carbodiimide as an activator. In another embodiment, the carbodiimide is selected from the group consisting of dicyclohexylcarbodiimide, diisopropylcarbodiimide, and N-(3-dimethylaminopropyl)-N'-ethylcarbodiimide-HCl.

In another embodiment in connection with the preparation of a compound of Formula V, the coupling agent comprises N-[(7-aza-1H-benzotriazol-1-yl)(dimethylamino)-methylene]-N-methylmethanaminium hexafluorophosphate N-oxide (HATU) as an activator.

In another embodiment in connection with the preparation of a compound of Formula V, the coupling agent comprises a carbodiimide as an activator and a base. In another embodiment, the base is 2,4,6-collidine, triethylamine, or diisopropylethylamine.

In another embodiment in connection with the preparation of a compound of Formula V, the coupling agent comprises a carbodiimide as an activator, a base, e.g., 2,4,6-collidine, and an additive. In one embodiment, the additive is OxymaPure® (also known ad ethyl cyano(hydroxyimino)acetate).

In another embodiment in connection with the preparation of a compound of Formula V, the solvent is selected from the group consisting of dichloromethane, N,N-dimethylformamide, tetrahydrofuran, 2-methyltetrahydrofuran, and N-methyl-2-pyrrolidone, In another embodiment, the solvent is dichloromethane.

In another embodiment in connection with the preparation of a compound of Formula V, the temperature is about 20° C. to about 45° C.

In another embodiment in connection with the preparation of the compound of Formula V, the stereomutation of a compound of Formula VI is less than about 10%. In another embodiment, the stereomutation of a compound having Formula VI is less than about 9%, about 8%, about 7%, about 6%, about 5%, about 4%, about 3%, about 2%, about 1%, or about 0.1%.

In another embodiment in connection with the preparation of the compound of Formula V, the compound of Formula V is obtained in about 95% ee or more (as determined by chiral HPLC). In another embodiment, the compound of Formula V is obtained in about 96% ee or more. In another embodiment, the compound of Formula V is obtained in about 97% ee or more. In another embodiment, the compound of Formula V is obtained in about 98% ee or more. In another embodiment, the compound of Formula V is obtained in about 99% ee or more.

In another embodiment in connection with the preparation of the compound of Formula V, the compound of Formula V is obtained in a chemical purity (as determined by HPLC) of about 95% or more. In another embodiment, the compound of Formula V is obtained in a chemical purity of about 96% or more. In another embodiment, the compound of Formula V is obtained in a chemical purity of about 97% or more. In another embodiment, the compound of Formula V is obtained in a chemical purity of about 98% or more. In another embodiment, the compound of Formula V is obtained in a chemical purity of about 99% or more.

In another embodiment, the disclosure provides a method of preparing a compound of Formula VI:

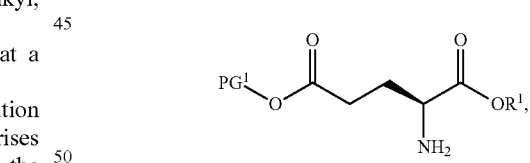

the method comprising reacting a compound of Formula VIII

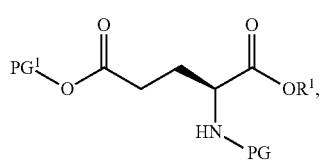

wherein:
$R^1$ is $C_1$-$C_4$ alkyl;
$PG^1$ is a protecting group; and
PG is a protecting group, with a deprotecting agent in a solvent at a temperature of about 0° C. to about 60° C., wherein the deprotecting agent selectively removes PG in the presence of PG¹.

In another embodiment in connection with the preparation of a compound of Formula VI, PG is selected from the group consisting of fluorenylmethyloxycarbonyl, tert-butyloxycarbonyl, and carboxybenzyl. In one embodiment, PG is fluorenylmethyloxycarbonyl and the amine deprotecting agent is selected from the group consisting of piperidine, diethylamine, triethylamine, and trimethylamine.

In another embodiment in connection with the preparation of a compound of Formula VI, PG is tert-butyloxycarbonyl and the amine deprotecting agent is selected from the group consisting of trifluoroacetic acid and hydrochloric acid.

In another embodiment in connection with the preparation of a compound of Formula VI, PG is carboxybenzyl and the amine deprotecting agent is hydrogen and the catalyst is palladium on carbon. In one embodiment, the pressure of hydrogen in connection with the preparation of a compound of Formula VI is about 1 to about 10 atm, about 1 to about 9 atm, about 1 to about 8 atm, about 1 to about 7 atm, about 1 to about 6 atm, about 1 to about 5 atm, about 1 to about 4 atm, about 1 to about 3 atm, about 1 to about 2 atm, or about 1 to about 1.5 atm.

In another embodiment, the method of preparing a compound of Formula VI further comprises a purification step, wherein the purification step comprises reacting a compound of Formula VI with an acid in a solvent to form a salt.

In another embodiment in connection with the purification of a compound of Formula VI, the acid is selected from L-tartaric acid and oxalic acid. In one embodiment, the acid is L-tartaric acid.

In another embodiment in connection with the purification of a compound of Formula VI, the reaction is carried out in isopropyl alcohol.

In another embodiment in connection with the purification of a compound of Formula VI, the purification step further comprises isolating the salt, e.g., by filtration.

In another embodiment in connection with the purification of a compound of Formula VI, the purification step further comprises neutralizing the salt to afford the free base of Formula VI. In one embodiment, the neutralization agent is a base. In one embodiment, the base is sodium bicarbonate.

In another embodiment in connection with the purification of a compound of Formula VI, the enantiomeric excess (ee) of the compound of Formula VI is improved by forming and then isolating the salt. The amount of improvement in ee depends on the ee of Formula VI before salt formation. For example, if the ee of Formula VI is about 50% or less before forming a salt, e.g., with a chiral acid such as L-tartaric acid, the ee may improve by about 49%, about 45%, about 40%, about 35%, about 30%, about 25%, about 20%, about 15%, or about 10% by forming and isolating the salt. If the ee of Formula VI is about 90% or more before forming a salt, e.g., with a chiral acid such as L-tartaric acid, the ee may improve by about 9%, about 8%, about 7%, about 6%, about 5%, about 4%, about 3%, about 2%, about 1%, or about 0.5% by forming and isolating the salt.

In another embodiment in connection with the purification of a compound of Formula VI, the chemical purity of the compound of Formula VI is improved by forming and then isolating the salt. The amount of improvement in chemical purity depends on the chemical purity of Formula VI before salt formation. For example, if the chemical purity of Formula VI is about 50% or less before forming a salt, the chemical purity may improve by about 49%, about 45%, about 40%, about 35%, about 30%, about 25%, about 20%, about 15%, or about 10% by forming and isolating the salt. If the chemical purity of Formula VI is about 90% or more before forming a salt, the chemical purity may improve by about 9%, about 8%, about 7%, about 6%, about 5%, about 4%, about 3%, about 2%, about 1%, or about 0.5% by forming and isolating the salt In another embodiment, the disclosure provides a method of preparing a compound of Formula VIII,

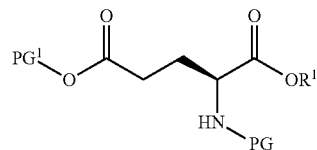

VIII the method comprising reacting a compound of Formula IX

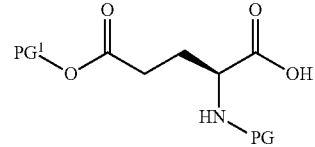

IX with $R^1$—OH, wherein:
$R^1$ is $C^1$-$C^4$ alkyl; and
in solvent, optionally, in the presence of an activator.

In another embodiment in connection with the preparation of a compound of Formula VIII, the activator is carbonyldiimidazole (CDI), hydroxybenzotriazole (HOBT), EDC, Amberlyst-15 ion, p-toluenesulfonic acid, and sulfuric acid. In one embodiment, the activator is CDI. In one embodiment, the equivalents of CDI in relationship to the compound of Formula IX is about 2.0, about 1.9, about 1.8, about 1.7, about 1.6, about 1.5, about 1.4, about 1.3, about 1.2, or about 1.1.

In another embodiment in connection with the preparation of a compound of Formula VIII, the solvent is selected from dichloromethane, acetonitrile, tetrahydrofuran, 2-methyltetrahydrofuran, and dimethylformamide. In one embodiment, the solvent is dichloromethane.

In another embodiment in connection with the preparation of a compound of Formula VIII, the reaction is carried out at a temperature of about 25° C. degree, about 20° C. degree, about 15° C. degree, about 10° C. degree, about 5° C. degree, or about 0° C. degree.

In another embodiment in connection with the preparation of the compound of Formula VIII, the stereomutation of a compound of Formula IX is less than about 10%. In another embodiment, the stereomutation of a compound having Formula IX is less than about 9%, about 8%, about 7%, about 6%, about 5%, about 4%, about 3%, about 2%, about 1%, or about 0.1%.

In another embodiment in connection with the preparation of the compound of Formula VIII, the compound of Formula VIII is obtained in about 95% ee or more (as determined by chiral HPLC). In another embodiment, the compound of Formula VIII is obtained in about 96% ee or more. In another embodiment, the compound of Formula VIII is obtained in about 97% ee or more. In another embodiment, the compound of Formula VIII is obtained in about 98% ee or more. In another embodiment, the compound of Formula VIII is obtained in about 99% ee or more.

In another embodiment in connection with the preparation of the compound of Formula VIII, the compound of Formula VIII is obtained in a chemical purity (as determined by HPLC) of about 95% or more. In another embodiment, the compound of Formula VIII is obtained in a chemical purity of about 96% or more. In another embodiment, the compound of Formula VIII is obtained in a chemical purity of about 97% or more. In another embodiment, the compound of Formula VIII is obtained in a chemical purity of about 98% or more. In another embodiment, the compound of Formula VIII is obtained in a chemical purity of about 99% or more.

In another embodiment, the disclosure provides a method of preparing Formulae I, II, III, V, VI, or VIII, wherein $R^1$ is isopropyl.

In another embodiment, the disclosure provides a method of preparing Formulae I I, II, III, or V, wherein $R^2$ is methyl.

In another embodiment, the disclosure provides a method of preparing Formulae I, II, III, or V, wherein $R^3$ is selected from the group consisting of:

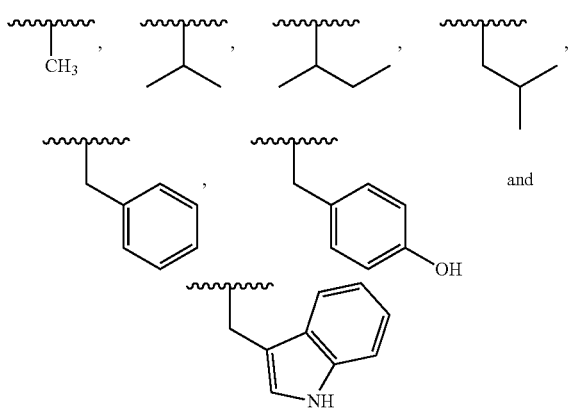

and

In another embodiment, $R^3$ is:

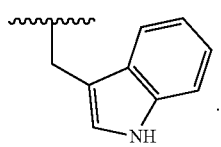 [SMILES: *Cc1c[nH]c2ccccc12]

In another embodiment, the disclosure provides a method of preparing isopropyl (S)-2-((S)-2-acetamido-3-(1H-indol-3-yl)propanamido)-6-diazo-5-oxohexanoate in a yield of about 10% or more, e.g., about 10%-90%, the method comprising reacting (S)-4-((S)-2-acetamido-3-(1H-indol-3-yl)propanamido)-5-isopropoxy-5-oxopentanoic (ethyl carbonic) anhydride with diazomethane in ether. In another embodiment, the yield is about 15% or more. In another embodiment, the yield is about 25% or more. In another embodiment, the yield is about 35% or more. In another embodiment, the yield is about 45% or more. In another embodiment, the yield is about 50% or more. In another embodiment, the yield is about 55% or more. In another embodiment, the yield is about 60% or more. In another embodiment, the yield is about 65% or more. In another embodiment, the yield is about 70% or more. In another embodiment, the yield is about 75% or more. In another embodiment, the yield is about 80% or more. In another embodiment, the yield is about 85% or more. In another embodiment, the yield is about 90% or more. In another embodiment, the yield is about 95% or more.

In another embodiment, the disclosure provides a method of preparing isopropyl (S)-2-((S)-2-acetamido-3-(1H-indol-3-yl)propanamido)-6-diazo-5-oxohexanoate in about 95% chemical purity or more, the method comprising reacting (S)-4-((S)-2-acetamido-3-(1H-indol-3-yl)propanamido)-5-isopropoxy-5-oxopentanoic (ethyl carbonic) anhydride with diazomethane in ether. In another embodiment, the chemical purity is about 96% or more. In another embodiment, the chemical purity is about 97% or more. In another embodiment, the chemical purity is about 98% or more. In another embodiment, the chemical purity is about 99% or more.

In another embodiment, the disclosure provides a method of preparing isopropyl (S)-2-((S)-2-acetamido-3-(1H-indol-3-yl)propanamido)-6-diazo-5-oxohexanoate in about 95% ee or more, the method comprising reacting (S)-4-((S)-2-acetamido-3-(1H-indol-3-yl)propanamido)-5-isopropoxy-5-oxopentanoic (ethyl carbonic) anhydride with diazomethane in ether. In another embodiment, the ee is about 96% or more. In another embodiment, the ee is about 97% or more. In another embodiment, the ee is about 98% or more. In another embodiment, the ee is about 99% or more.

In another embodiment, the disclosure provides a method of preparing a compound of Formula I from a compound of Formula IX according to Scheme 13.

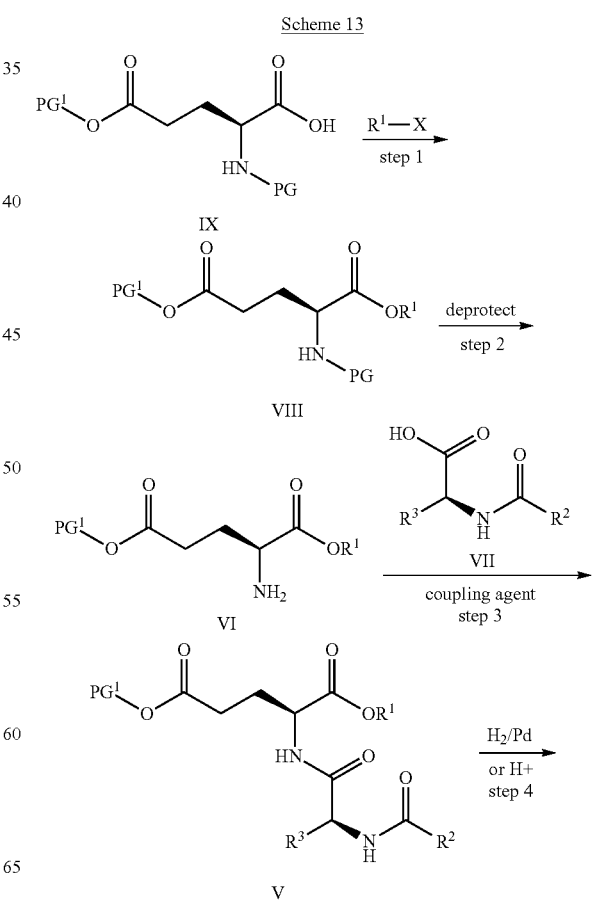

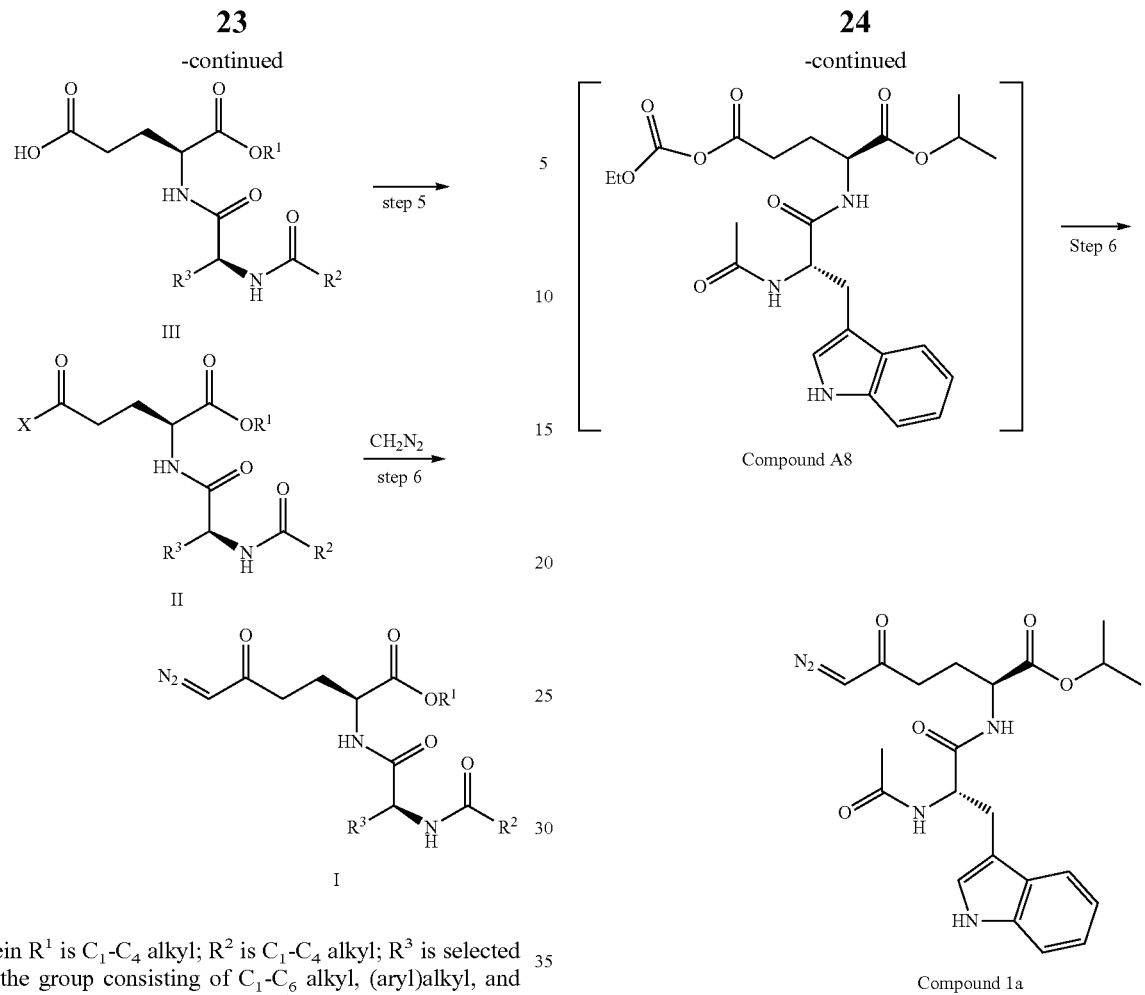

wherein $R^1$ is $C_1$-$C_4$ alkyl; $R^2$ is $C_1$-$C_4$ alkyl; $R^3$ is selected from the group consisting of $C_1$-$C_6$ alkyl, (aryl)alkyl, and (heteroaryl)alkyl; and PG and $PG^1$ are protecting groups, and the reagents and conditions of steps 1-6 are described above in connection with the preparation of Formulae I, II, III, V, and VIII.

In another embodiment, the disclosure provides a method of preparing Compound 1a according to Scheme 13A, wherein the reagents and conditions of steps 5 and 6 are described above in connection with the preparation of Formulae I and II.

In another embodiment, the disclosure provides a method of preparing Compound 1a according to Scheme 13B.

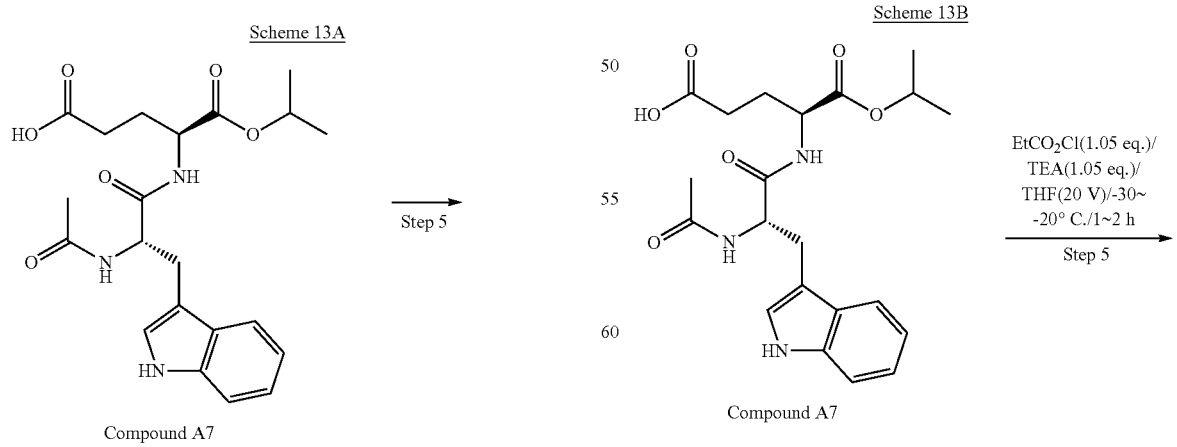

25
-continued

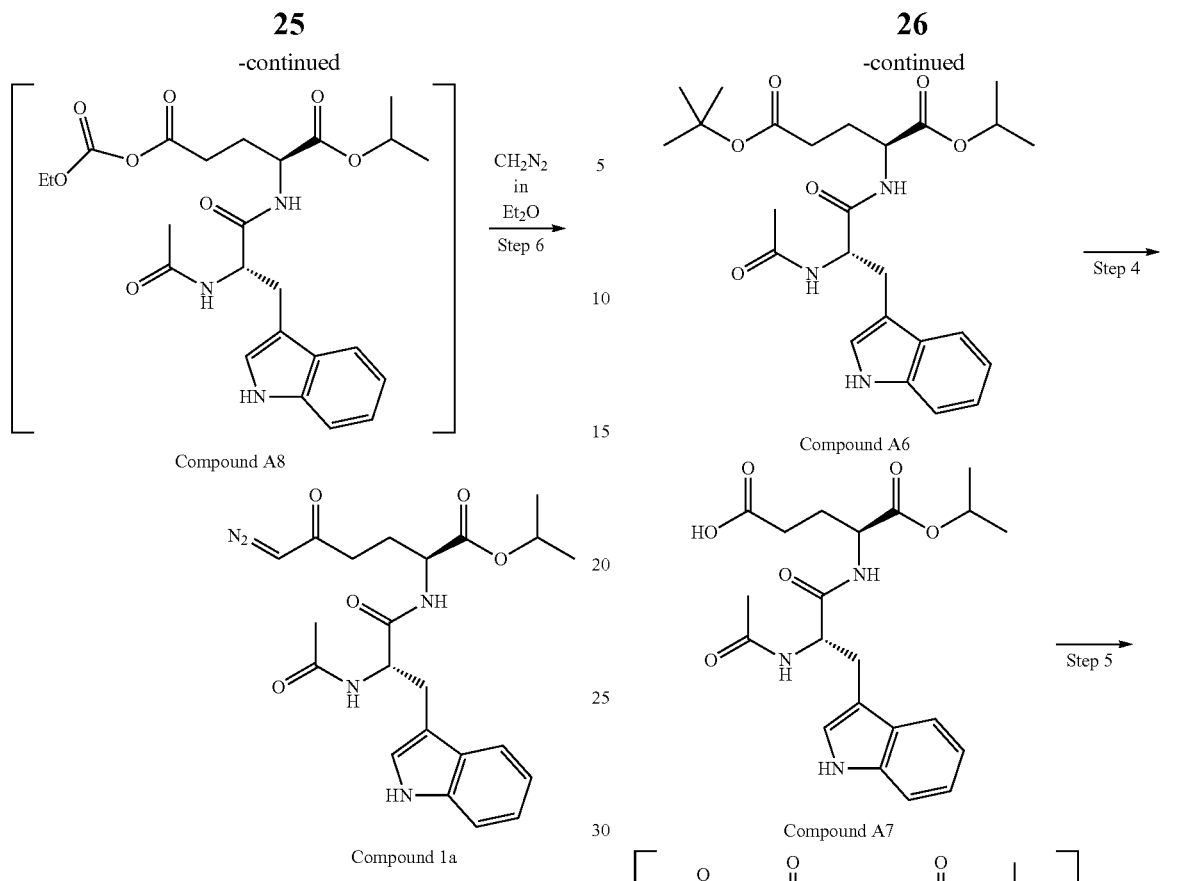

Compound A8

Compound 1a

In another embodiment, the disclosure provides a method of preparing Compound 1a according to Scheme 13C, wherein the reagents an conditions of steps 1-6 are described above in connection with the preparation of Formulae I, II, III, V, and VIII.

Scheme 13C

SM1

Compound A1

Compound A3-L-tartaric acid salt

26
-continued

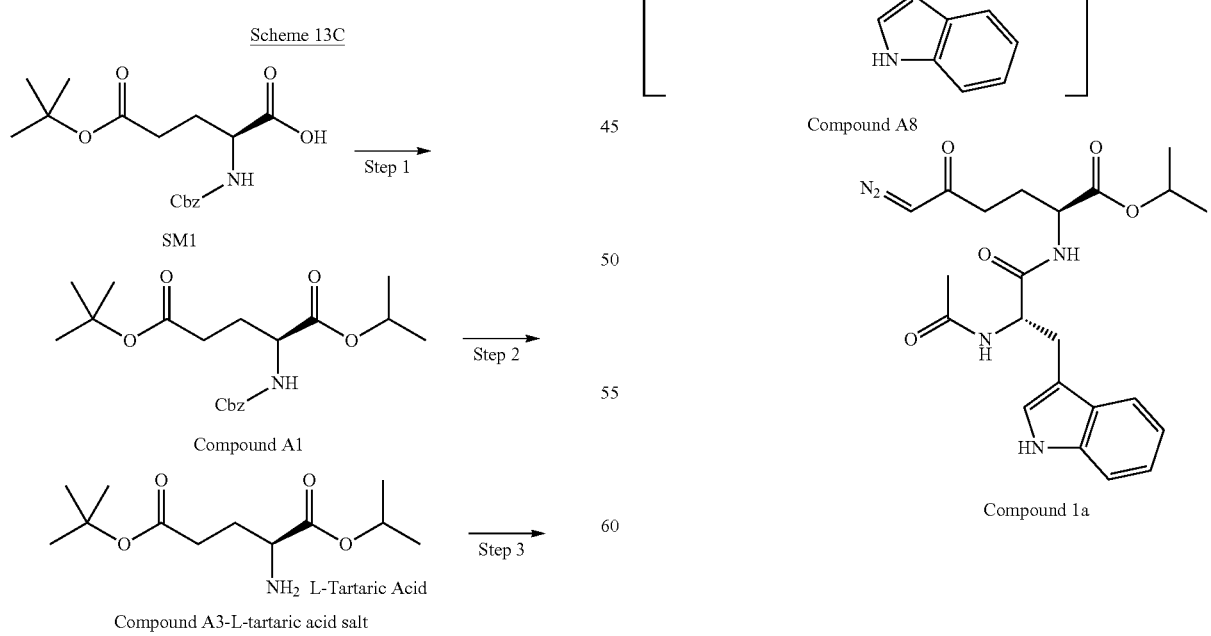

Compound A6

Compound A7

Compound A8

Compound 1a

In another embodiment, the disclosure provides a method of preparing Compound 1a according to Scheme 13D.

Scheme 13D

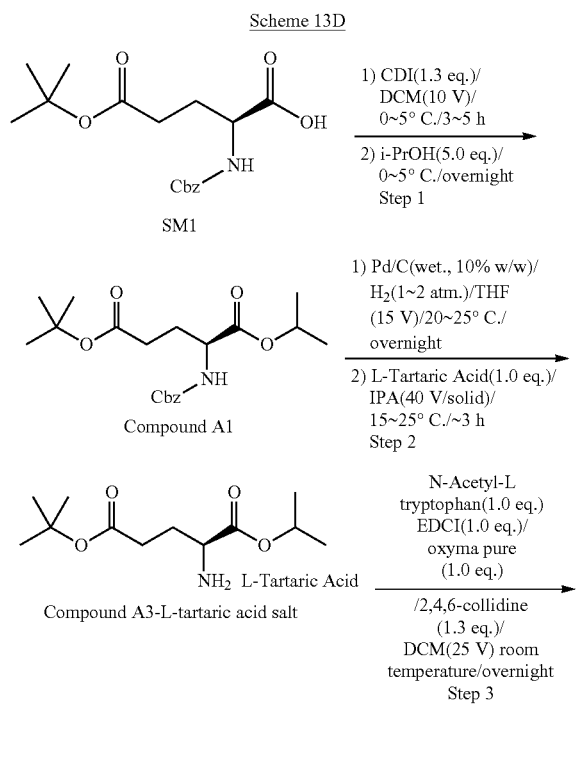

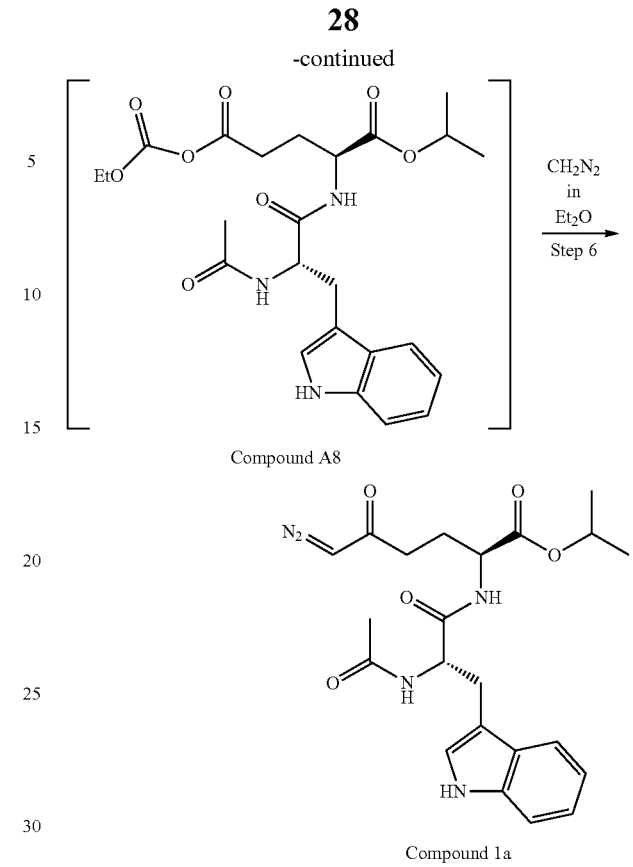

In another embodiment, the disclosure provides a method of improving the chemical purity and/or ee of a compound of Formula VI, comprising forming a salt of Formula VI, and isolating the salt.

In one embodiment, the chemical purity is improved by about 1% or more In one embodiment, the chiraly purity, e.g., the ee, is improved by about 1% or more. In another embodiment, the salt is formed using a chiral acid, e.g., L-tartaric acid. In another embodiment, the salt is formed using an achiral acid, e.g., oxalic acid. The isolated salt of Formula VI can be converted back to the free-base of Formula VI by treatment with a base, e.g., $NaHCO_3$, according to Scheme 14.

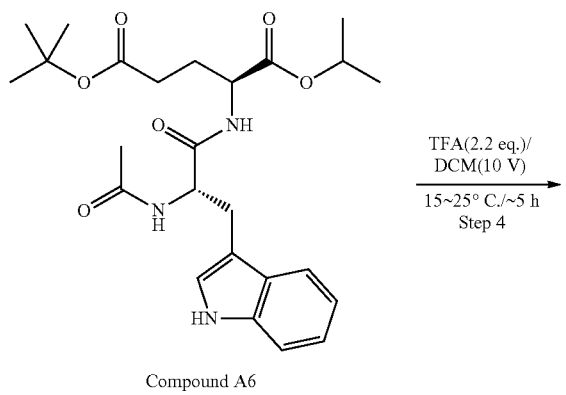

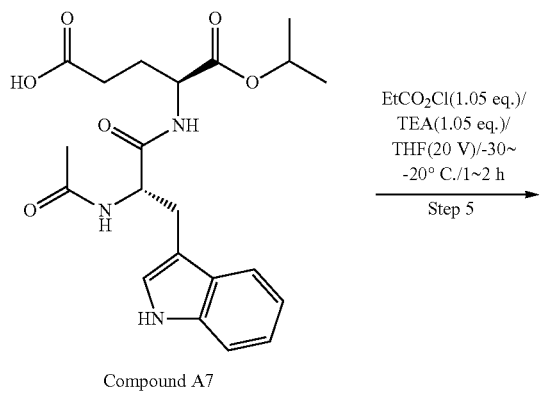

Scheme 14

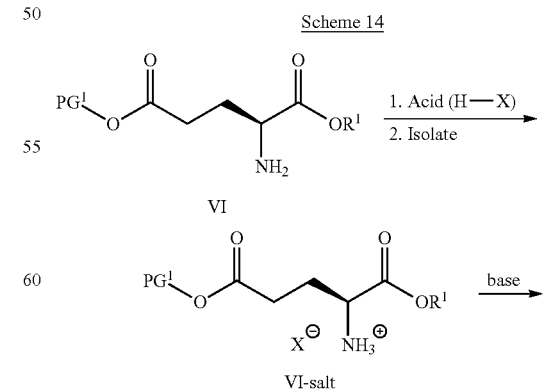

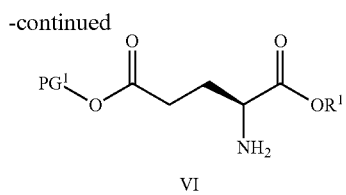

VI

Definitions

The term "halo" as used herein by itself or as part of another group refers to —Cl, —F, —Br, or —I.

The term "nitro" as used herein by itself or as part of another group refers to —NO$_2$.

The term "cyano" as used herein by itself or as part of another group refers to —CN.

The term "hydroxy" as herein used by itself or as part of another group refers to —OH.

The term "amino acid" represents natural or non-natural amino acids. Natural amino acids include acids used for protein biosynthesis, as well as other amino acids that can be incorporated into proteins during translation (including pyrrolysine and selenocysteine) or amino acids which are formed during intermediary metabolism (such as ornithine). Non-natural amino acids are in particular amino acids arising from modification of the natural amino acids, e.g., by addition of protecting groups, or by substitution of a hydrogen in the side chain of the amino acid by, for example, $C_1$-$C_6$ alkyl, —OH, —SH, —NH$_2$, —NH($C_1$-$C_6$ alkyl), —NO$_2$, halogen, $C_6$-$C_{10}$aryl, $C_3$-$C_8$ heteroaryl, or $C_3$-$C_8$ cycloalkyl (e.g., S-methyl methionine), or by oxidation of functional groups (e.g., sulfoxidation in a sulfur-containing amino acid). Non-natural amino acids include also homologues or analogues of natural amino acids, such as pyroglutamine, homocitrulline, homoarginine, homoserine, homotyrosine, homoproline, or homophenylalanine.

Examples of non-proteinogenic acids include: citrulline, hydroxyproline, 4-hydroxyproline, beta-hydroxyvaline, ornithine, beta-amino alanine, albizziin, 4-aminophenylalanine, biphenylalanine, 4-nitro-phenylalanine, 4-fluoro-phenylalanine, pentafluorophenylalanine, norleucine, cyclohexylalanine, selenomethionine, lanthionine, dehydroalanine, naphthylalanine, tert-leucine, tert-butylalanine, cyclopropylglycine, cyclohexylglycine, diethylglycine, or dipropylglycine.

An "amino acid side chain" is a moiety present in amino acids and bound to their alpha-carbon. Amino acids generally are compounds containing a carboxylic group, an amino group, and an alpha-carbon to which both the carboxylic group and the amino group are bound.

By way of example, the side chains of natural amino acids include:

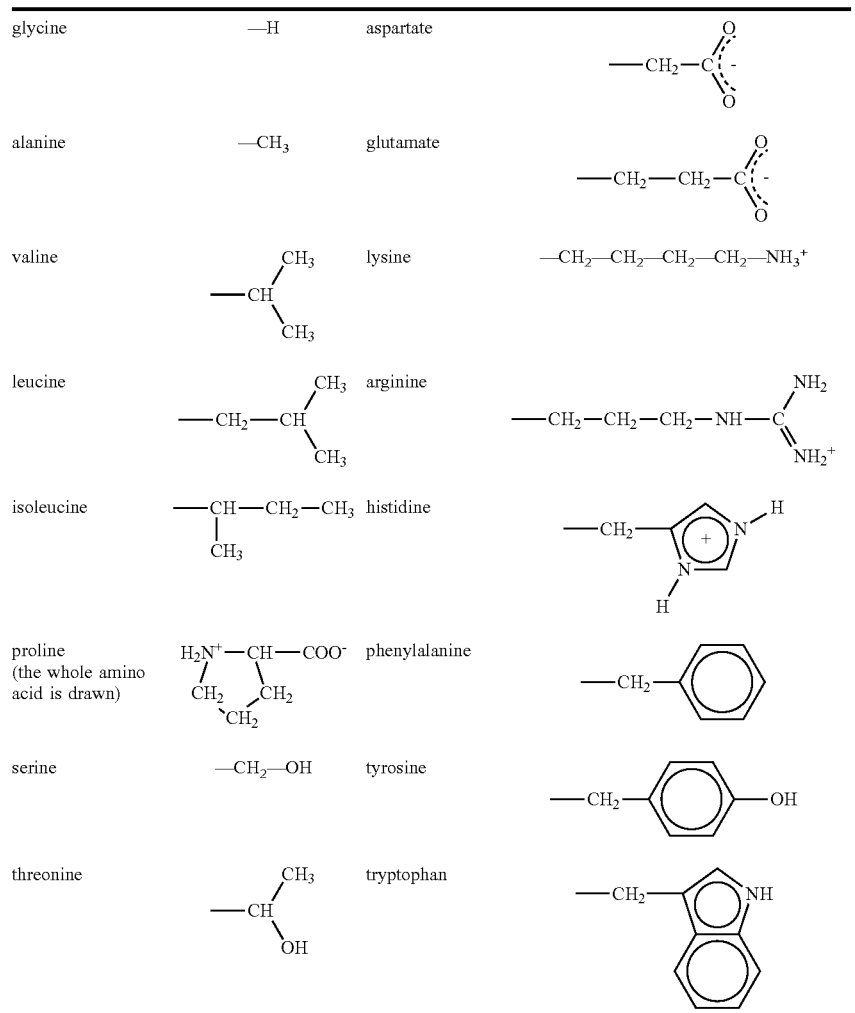

| | | | |
|---|---|---|---|
| cysteine | —CH₂—SH | asparagine | 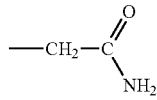 |
| methionine | —CH₂—CH₂—S—CH₃ | glutamine | 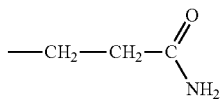 |

The term "alkyl" as used herein by itself or as part of another group refers to a straight- or branched-chain aliphatic hydrocarbon containing one to eight carbon atoms, i.e., a $C_1$-$C_8$ alkyl, or the number of carbon atoms designated, e.g., a $C_1$ alkyl such as methyl, a $C_2$ alkyl such as ethyl, etc. In one embodiment, the alkyl is a $C_1$-$C_8$ alkyl. In another embodiment, the alkyl is a $C_1$-$C_6$ alkyl. In another embodiment, the alkyl is a $C_3$-$C_6$ alkyl. In another embodiment, the alkyl is a $C_1$-$C_4$ alkyl, i.e., methyl, ethyl, propyl, isopropyl, butyl, isobutyl, or tert-butyl.

The term "alkoxy" as used herein by itself or as part of another group refers to an alkyl group attached to a terminal oxygen atom. In one embodiment, the alkyl is a $C_1$-$C_4$ alkyl group. Non-limiting exemplary alkoxy groups include methoxy, ethoxy, and tert-butoxy.

The term "(aryl)alkyl" as used herein by itself or as part of another group refers to an alkyl substituted with one optionally substituted aryl group. In one embodiment, the aryl is an optionally substituted phenyl. In another embodiment, the alkyl is a $C_1$-$C_4$ alkyl. In another embodiment, the alkyl is a $C_1$ or $C_2$ alkyl. Non-limiting exemplary (aryl)alkyl groups include benzyl and 4-OH-benzyl.

The term "aryl" as used herein by itself or as part of another group refers to an aromatic monocyclic or polycyclic hydrocarbyl group having 6 to 10 carbon atoms. The cycles can be fused. In one embodiment, the term aryl refers to phenyl (abbreviated as "Ph") or naphthyl groups. In another embodiment, the aryl group is phenyl.

The term "optionally substituted aryl" as used herein by itself or as part of another group refers to a phenyl or naphthyl groups that is either unsubstituted or substituted with one to five substituents, wherein the substituents are each independently halo, nitro, cyano, hydroxy, —$NH_2$, $C_1$-$C_4$ alkyl, or $C_1$-$C_4$ alkoxy. Non-limiting exemplary optionally substituted aryl groups include 4-fluorophenyl and 4-OH-phenyl, The term "(heteroaryl)alkyl" as used herein by itself or as part of another group refers to an alkyl substituted with one optionally substituted 5- to 14-membered heteroaryl group. In one embodiment, the alkyl group is substituted with one optionally substituted 5- to 9-membered heteroaryl group. In another embodiment, the alkyl group is a $C_1$-$C_4$ alkyl. In another embodiment, the alkyl group is a $C_1$ or $C_2$ alkyl.

The term "heteroaryl" as used herein by itself or as part of another group refers to monocyclic and bicyclic aromatic ring systems having five to 14 fourteen ring members, i.e., a 5- to 14-membered heteroaryl, comprising one, two, three, or four heteroatoms, or the number of ring members specified, e.g., a 5- to 8-membered hetereoaryl. Each heteroatom is independently oxygen, sulfur, or nitrogen. In one embodiment, the heteroaryl has three heteroatoms. In another embodiment, the heteroaryl has two heteroatoms. In another embodiment, the heteroaryl has one heteroatom. In another embodiment, the heteroaryl is a 5- to 9-membered heteroaryl. Non-limiting exemplary heteroaryl groups include thienyl, pyrrolyl, imidazolyl, pyrazolyl, indolyl, and indazolyl.

The term "optionally substituted heteroaryl" as used herein by itself or as part of another group refers to a heteroaryl that is either unsubstituted or substituted with one to four substituents, wherein the substituents are independently halo, nitro, cyano, hydroxy, —$NH_2$, $C_1$-$C_4$ alkyl, or $C_1$-$C_4$ alkoxy.

The term "coupling agent" as used herein refers to the reagent, e.g., activator, or combination of reagents, e.g., activator and base, or activator, base, and additive(s), used to form an amide bond between a carboxylic acid and an amine. Coupling agents are well known in the art. Any coupling agent known in art can be used in the amide bond forming reaction between a compound of Formula VI and a compound of Formula VII, or the compound of Formula (4) and an amino acid or protected amino acid, so long as the coupling agent causes stereomutation of the starting materials in an amount of less than about 6%. In another embodiment, the coupling agent causes stereomutation of the starting materials in an amount of less than about 5%. In another embodiment, the coupling agent causes stereomutation of the starting materials in an amount of less than about 4%. In another embodiment, the coupling agent causes stereomutation of the starting materials in an amount of less than about 3%. In another embodiment, the coupling agent causes stereomutation of the starting materials in an amount of less than about 2%. In another embodiment, the coupling agent causes stereomutation of the starting materials in an amount of less than about 1%.

In one embodiment, the coupling agent comprises and activator, e.g., a carbodiimide (dicyclohexylcarbodiimide, diisopropylcarbodiimide, (N-(3-dimethylaminopropyl)-N'-ethylcarbodiimide·HCl) or (N-[(7-Aza-1H-benzotriazol-1-yl)(dimethylamino)-methylene]-N-methylmethanaminium hexafluorophosphate N-oxide (HATU). In another embodiment, the coupling agent comprises and activator, e.g., a carbodiimide, and a base, e.g., 2,4,6-collidine. In another embodiment, the coupling agent comprises and activator, e.g., a carbodiimide, a base, e.g., 2,4,6-collidine, and at least one additive, e.g., 1-hydroxybenzotriazole or OxymaPure®.

The term "protecting group" as used herein refers to group that blocks, i.e., protects, an amine, hydroxy, and/or carboxy functionality while reactions are carried out on other functional groups or parts of the molecule. Those skilled in the art will be familiar with the selection, attachment, and cleavage of protecting groups and will appreciate that different protective groups are known in the art, the suitability of one protective group or another being dependent on the particular the synthetic scheme planned. Treatises on the subject are available for consultation, such as Wuts, "Greene's Protective Groups in Organic Synthesis", 5th Ed., J. Wiley & Sons, Inc., NY, 2014. Suitable amine protecting groups include, but are not limited to, carbobenzyloxy (Cbz), tert-butyloxycarbonyl (BOC), 9-fluorenylmethyloxycarbonyl (FMOC), and benzyl (Bn) groups. Suitable hydroxy protecting groups include, but are not limited to t-butyldimethylsilyl (TBDMS), trimethylsilyl (TMS), and other silyl-based groups, benzyl (Bn), allyl, methoxymethyl (MOM), and tetrahydropyranyl (THP) groups. Suitable carboxy protecting groups include, but are not limited to methyl, t-butyl, and benzyl groups.

The term "cycloalkyl" designates a saturated cyclic hydrocarbyl group, which may be monocyclic or polycyclic, and the cycles can be fused. Examples of cycloalkyls are cyclopropyl, cyclobutyl, cyclopentyl, cyclohexyl, or adamantyl.

The term "heterocycloalkyl" is an aliphatic cyclic group containing carbon atoms, typically 3-10 carbon atoms, and at least one heteroatom which is selected from O, S, or N in addition to the carbon atoms. The heterocycloalkyl may be monocyclic or polycyclic, and the cycles can be fused. Examples include pyrrolidone, piperidine, quinuclidine, 1-azaadamantane, azetidine, tetrahydrofurane, morpholine, or thiomorpholine.

The term "heteroalkyl" is an aliphatic linear or branched group containing carbon atoms, typically 3-8 carbon atoms, and at least one heteroatom which is selected from O, S, or N in addition to the carbon atoms.

The above alkyl, cycloalkyl, heterocycloalkyl, and heteroalkyl groups may optionally be substituted. The substituents include halogen, $C_1$-$C_4$ alkyl, $C_1$-$C_4$ hydroxyalkyl, $C_1$-$C_4$ alkyloxy, $C_1$-$C_4$ mercaptoalkyl, $C_1$-$C_4$ alkylmercapto, amino($C_1$-$C_4$)alkyl, dimethylamino($C_1$-$C_4$)alkyl, $C_1$-$C_4$ alkylamino, $C_1$-$C_4$ dialkylamino, wherein the alkyls are the same or different, carboxy, $C_1$-$C_4$-alkyloxycarbonyl, $C_1$-$C_5$ acyl, $C_1$-$C_5$ acyloxy, nitro, or phenyl.

The term "precursor of $R^3$" shall be understood as a moiety which upon chemical modification yields the moiety $R^3$. Typically, the chemical modification is a one-step or a two-step reaction. Most preferably, the precursor of $R^3$ is a moiety $R^3$ provided with a protecting group, and the chemical modification is deprotection.

The term "base" as used herein refers to an organic proton acceptor. Non-limiting bases include non-nucleophilic tertiary amines, e.g., $NEt_3$ $iPr_2NEt$, N-methylmorpholine, and nitrogen-containing heteroaromatic groups such as pyridine, and derivatives of pyrindine, e.g., 2,4,6-collidine.

The term "acetyl-L-tryptophan" as used herein refers to a compound having the following structure:

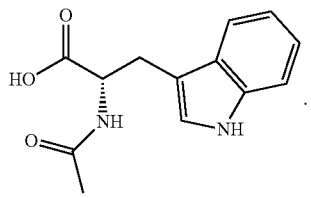 [SMILES: CC(=O)N[C@@H](Cc1c[nH]c2ccccc12)C(=O)O]

The term "isopropyl (S)-2-amino-6-diazo-5-oxohexanoate" as used herein refers to a compound having the following structure:

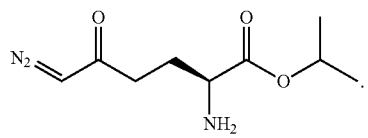

The term "stereomutation" as used herein refers to a change of configuration at a chiral center brought about by chemical means.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "absolute configuration" refers to the spatial arrangement of the atoms of a chiral molecular entity (or group) and its stereochemical description, e.g., R or S.

The stereochemical terms and conventions used in the specification are meant to be consistent with those described in *Pure & Appl. Chem* 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry.

The term "chiral purity" as used herein refers the amount of one enantiomer in a mixture of two enantiomers based on the weight fraction, e.g., peak area percentage from chiral HPLC analysis, of the predominant enantiomer. For example, if a compound mixture contains is 98.2% of the R-isomer and 1.8% of the S-isomer, the chiral purity of the mixture is 98.2%. The ee is 96.4%.

The terms "a" and "an" refer to one or more than one.

The term "about," as used herein, includes the recited number ±10%. Thus, "about 10" means 9 to 11.

The following abbreviations may be used:

| | |
|---|---|
| eq. | Equivalent(s) |
| Kg | Kilogram(s) |
| g | gram(s) |
| h | Hour(s) |
| HPLC | high-performance liquid chromatography |
| LCMS | liquid chromatography mass spectrometry |
| mL | milliliter |
| Temp. | temperature |
| THF | tetrahydrofuran |

| | |
|---|---|
| DCM | dichloromethane |
| GC | Gas Chromatography |
| DMF | N,N-dimethylformamide |
| NMP | 1-methylpyrrolidin-2-one |
| atm. | Standard atmospheric pressure |
| TEA | triethylamine |
| V | volume |
| ACN | acetonitrile |
| SM | Starting Material |
| MTBE | 2-methoxy-2-methylpropane |
| IPA | propan-2-ol |
| EtOAc | ethyl acetate |
| DMSO | Dimethyl sulfoxide |

EXAMPLE 1

Synthesis of 5-Benzyl 1-isopropyl (tert-butoxycarbonyl)-L-glutamate (3a)

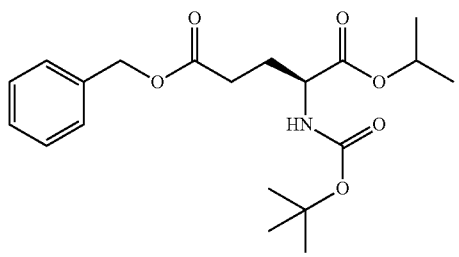 [SMILES: CC(C)OC(=O)[C@H](CCC(=O)OCc1ccccc1)NC(=O)OC(C)(C)C]

Compound 3a was prepared according to known literature procedure (Hobbs, M. J.; Williams, N. E.; Patel, S. K.; Upshall, D. G. *Biochem. Pharm.* 1998, 55, 1573). The reaction conditions were: 2-bromopropane, DBU, TBAI, THF, reflux, 13 h. $^1$H and $^{13}$C NMR spectra were in agreement with the published data.

EXAMPLE 2

Synthesis of(S)-5-(Benzyloxy)-1-isopropyl-1,5-dioxopentan-2-aminium 2,2,2-trifluoroacetate

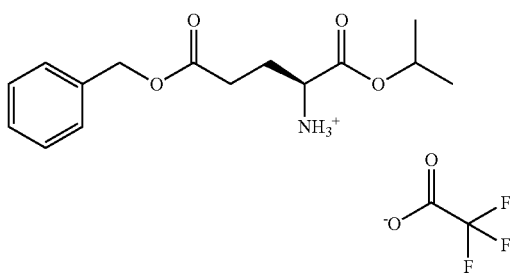

Compound 4a was prepared according to known literature procedure (Bitta, J.; Kubik, S. *Org. Lett.* 2001, 3, 2637). The reaction conditions were: DCM/TFA 1:1, r.t., 2 h. $^1$H and $^{13}$C NMR spectra were in agreement with the published data.

EXAMPLE 3

Synthesis of 5-Benzyl 1-isopropyl(((9H-fluoren-9-yl)methoxy)carbonyl)-L-tryptophyl-L-glutamate (5b)

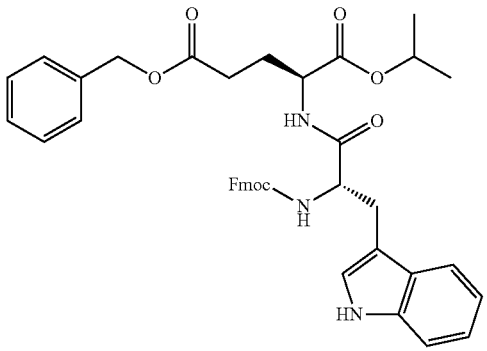

Fmoc-L-Trp-OH (986 mg, 2.31 mmol, 1 equiv.) and HATU (1.01 g, 2.66 mmol, 1.15 equiv) were suspended in DCM (30 mL) under an inert atmosphere. The reaction mixture was cooled to 0° C. and DIEA (1.49 g, 2.01 mL, 11.6 mmol, 3 equiv.) was added. Finally the solution of compound 4a (1.00 g, 2.54 mmol, 1.1 equiv.) in DCM (5 mL) was dropwise added during 5 minutes. The resulting mixture was stirred for 15 minutes at 0° C. and for 2 h at room temperature. Further DCM (35 mL) was added and reaction mixture was washed with sat. NaHCO$_3$ (50 mL), distilled H$_2$O (50 mL), 1M HCl (50 mL), distilled H$_2$O (50 mL), sat. NaCl (50 mL) and dried over anhydrous MgSO$_4$. DCM was evaporated and the crude product (1.59 g, a quantitative yield) was used to the following step without further purification.

$^1$H NMR (401 MHz, CDCl$_3$): $\delta_H$ 1.19 (d, J=6.1, 3H), 1.22 (d, J=5.8, 3H), 1.87 (q, J=10.0, 9.2, 1H), 2.32-2.04 (m, 3H), 3.14 (dd, J=14.5, 7.1, 1H), 3.41 (d, J=16.0, 1H), 4.20 (t, J=7.0, 1H), 4.37 (d, J=7.4, 1H), 4.40-4.50 (m, 2H), 4.51-4.58 (m, 1H), 4.99-4.88 (m, 1H), 5.06 (bs, 2H), 5.46 (d, J=7.7, 1H), 6.44 (d, J=7.3, 1H), 7.04 (bs, 1H), 7.13 (t, J=7.4, 1H), 7.18 (t, J=7.2, 1H), 7.43-7.26 (m, 10H), 7.62-7.50 (m, 2H), 7.65 (d, J=7.9, 1H), 7.76 (d, J=7.6, 2H), 7.95 (s, 1H).

$^{13}$C NMR (101 MHz, DMSO-d$_6$): $\delta_C$ 21.5, 21.5, 26.0, 27.7, 29.8, 46.6, 51.4, 65.5, 65.6, 68.1, 110.2, 111.3, 118.2, 118.5, 120.1 (2C), 120.8, 123.9, 125.3, 125.3, 127.0 (2C), 127.2, 127.6 (2C), 127.8 (2C), 127.9 (2C), 128.4 (2C), 136.1, 136.1, 140.5, 140.6, 143.7, 143.8, 155.8, 171.0, 172.1, 172.4.

Optical rotation: $[\alpha]^{22}_D$ –30.2° (c 0.305; DMF).

IR (KBr): 3517, 3430, 3402, 3295, 3064, 3039, 1726, 1717, 1697, 1673, 1653, 1610, 1586, 1537, 1517, 1499, 1458, 1451, 1388, 1373, 1343, 1271, 1249, 1189, 1173, 1105, 1081, 1067, 1031, 1009, 757, 736, 697, 608 cm$^{-1}$.

ESI MS: 710.3 ([M+Na]$^+$).

HR ESI MS: Calcd. for C$_{41}$H$_{42}$O$_7$N$_3$ 688.30173. Found: 688.30219.

EXAMPLE 4

Synthesis of 5-Benzyl 1-isopropyl ((benzyloxy)carbonyl)-L-tryptophyl-L-glutamate (5a)

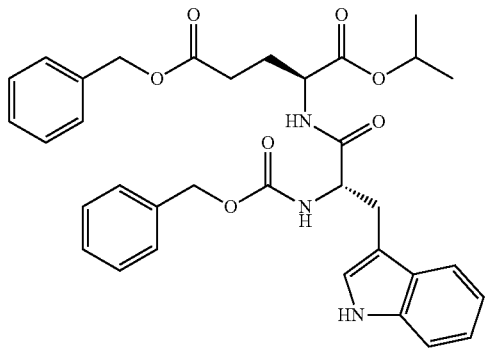 [SMILES: CC(C)OC(=O)[C@H](CCC(=O)OCc1ccccc1)NC(=O)[C@H](Cc1c[nH]c2ccccc12)NC(=O)OCc1ccccc1]

Z-Trp-OH (2.12 g, 6.27 mmol, 1.1 equiv.) and HATU (2.50 g, 6.58 mmol, 1.15 equiv.) were suspended in DCM (15 mL) under an inert atmosphere. The reaction mixture was cooled to 0° C. and DIEA (3.00 mL, 17.1 mmol, 3.0 equiv.) was added. Finally, a solution of compound 4a (1.60 g, 5.70 mmol, 1.0 equiv.) in DCM (10 mL) was added. The resulting mixture was stirred for 15 min. at 0° C. and overnight at room temperature. Then, solvent was evaporated, EtOAc was added (150 mL) and the organic phase was washed with distilled $H_2O$ (100 mL), 10% aq. $KHSO_4$ (2×100 mL), sat. $NaHCO_3$ (2×100 mL) and brine (100 mL). The organic phase was then dried over anhydrous $MgSO_4$ and solvent was evaporated. The residue was crystallized from MeOH to afford 2.82 g (83%) of product as colorless needles.

$^1$H NMR (401 MHz, $CDCl_3$): $\delta_H$ 1.21 (dd, J=14.6, 7.0, 6H), 1.78-1.91 (m, 1H), 2.04-2.26 (m, 3H), 3.15 (dd, J=14.6, 7.0, 1H), 3.39 (dd, J=15.1, 4.7, 1H), 4.45 (td, J=7.7, 3.3, 1H), 4.50-4.58 (m, 1H), 4.94 (p, J=6.3, 1H), 5.07 (s, 2H), 5.11 (d, J=6.5, 2H), 5.41 (d, J=8.7, 1H), 6.45 (d, J=7.5, 1H), 7.03 (s, 1H), 7.09 (t, J=7.4, 1H), 7.16 (td, J=8.1, 1.2, 1H), 7.24-7.41 (m, 11H), 7.62 (d, J=7.8, 1H), 7.98 (s, 1H).

$^{13}$C NMR (101 MHz, $CDCl_3$): $\delta_C$ 21.8 (2C), 27.4, 28.3, 30.0, 52.0, 55.8, 66.6, 67.2, 69.6, 110.2, 111.4, 118.8, 120.0, 122.4, 123.6, 127.6, 128.2, 128.3, 128.5 (2C), 128.7, 128.8, 135.9, 136.3, 156.1, 170.7, 171.3, 172.6.

Optical rotation: $[\alpha]^{22}_D$ −29.7° (c 0.279; DMF).

IR (KBr): 3515, 3411, 3301, 3064, 1735, 1725, 1696, 1653, 1587, 1546, 1535, 1521, 1499, 1456, 1416, 1388, 1374, 1331, 1271, 1249, 1234, 1184, 1173, 1106, 1082, 1065, 1028, 1011, 758, 740, 697, 605 $cm^{-1}$.

ESI MS: 622.3 ($[M+Na]^+$).

HR ESI MS: Calcd. for $C_{34}H_{37}O_7N_3Na$ 622.25237; found 622.25250.

EXAMPLE 5

Synthesis of 5-Benzyl 1-isopropyl acetyl-L-tryptophyl-L-glutamate (5c)

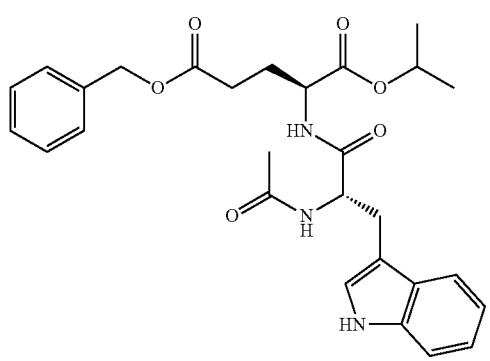 [SMILES: CC(=O)N[C@@H](Cc1c[nH]c2ccccc12)C(=O)N[C@@H](CCC(=O)OCc1ccccc1)C(=O)OC(C)C]

Compound 4a (1.17 g, 1.70 mmol, 1 equiv) was suspended in anhydrous DCM (9 mL). DMAP (1.45 g, 11.9 mmol, 7 equiv) followed by AcOSu (2.14 g, 13.6 mmol, 8 equiv.) were added and the resulting mixture became clear (yellow-orange solution). The resulting mixture was stirred at room temperature for 69 h under an inert atmosphere. Further DCM (100 mL) was added and organic phase was washed with 1M HCl (2×100 mL), distilled $H_2O$ (100 mL), sat. $NaHCO_3$ (100 mL), distilled $H_2O$ (100 mL), sat. NaCl (100 mL) and dried over anhydrous $MgSO_4$. The DCM was evaporated and the crude product was purified by column chromatography ($CHCl_3$/MeOH 15:1, $R_f$=0.37) to obtained a colorless solid (803 mg, 93%).

$^1$H NMR (401 MHz, DMSO-$d_6$): $\delta_H$ 1.16 (d, J=6.2, 3H), 1.18 (d, J=6.2, 3H), 1.74 (s, 3H), 1.87 (dtd, J=13.8, 8.8, 6.2, 1H), 2.03 (dddd, J=13.7, 8.7, 7.1, 5.2, 1H), 2.44 (ddd, J=8.6, 6.7, 5.0, 2H), 2.87 (dd, J=14.8, 9.7, 1H), 3.10 (dd, J=14.7, 4.2, 1H), 4.25 (ddd, J=9.2, 7.4, 5.2, 1H), 4.56 (ddd, J=9.7, 8.2, 4.3, 1H), 4.90 (hept, J=6.3, 1H), 5.10 (bs, 2H), 6.97 (ddd, J=8.0, 7.0, 1.1, 1H), 7.05 (ddd, J=8.1, 6.9, 1.2, 1H), 7.14 (d, J=2.3, 1H), 7.33-7.30 (m, 1H), 7.41-7.33 (m, 5H), 7.61 (dd, J=7.7, 1.0, 1H), 8.03 (d, J=8.2, 1H), 8.43 (d, J=7.5, 1H), 10.80 (d, J=2.4, 1H).

$^{13}$C NMR (101 MHz, DMSO-$d_6$): $\delta_C$ 21.5, 21.5, 22,5, 25.9, 27,8, 29.8, 51.4, 53.0, 65.5, 68.0, 110.2, 111.3, 118.1, 118.4, 120.8, 123.6, 127.3 (2C), 127.9, 128.0 (2C), 128.4, 136.0, 136.1, 169.0, 171.0, 172.1, 172.2.

Optical rotation: $[\alpha]^{22}_D$ −22.1° (c 0.294; DMF).

IR (KBr): 3408, 3290, 3080, 3065, 3037, 1736, 1725, 1718, 1680, 1660, 1643, 1620, 1586, 1547, 1522, 1499, 1457, 1417, 1387, 1373, 1345, 1279, 1251, 1183, 1172, 1107, 1070, 1031, 915, 757, 741, 697, 598 cm 1.

ESI MS: 530.2 ($[M+Na]^+$).

HR ESI MS: Calcd. for $C_{28}H_{33}O_6N_3Na$ 530.22616. Found: 530.22674.

EXAMPLE 6

Synthesis of (S)-4-((S)-2-Acetamido-3-(1H-indol-3-yl)propanamido)-5-isopropoxy-5-oxopentanoic acid (6a)

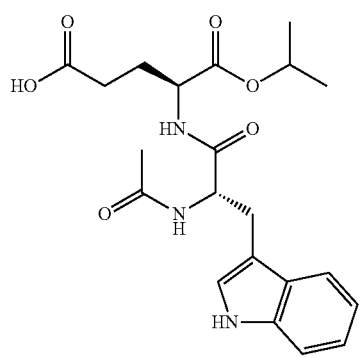 [SMILES: CC(=O)N[C@@H](Cc1c[nH]c2ccccc12)C(=O)N[C@@H](CCC(=O)O)C(=O)OC(C)C]

Procedure starting with compound 5c: Compound 5c (172 mg, 0.339 mmol, 1 equiv.) and 10% Pd/C (36 mg, 0.034 mmol, 0.1 equiv) were dissolved in anhydrous THF (10 mL). The reaction mixture was saturated with $H_2$ and stirred under a $H_2$ atmosphere overnight (18 h). The precipitate was filtered and filtrate was washed with further THF (2×10 mL). The solvent was evaporated and compound 6a was obtained as a colorless solid (106 mg) in 75% yield.

Procedure Starting with Compound 5a:

Compound 5a (0.6 g, 1.00 mmol, 1 equiv.) was dissolved in anhydrous THF (20 mL) under an inert atmosphere, 10% Pd/C (0.12 g, 0.11 mmol, 0.11 equiv.) and $Ac_2O$ (95 μL; 1.00 mmol, 1 equiv.) were added. The reaction mixture was saturated with $H_2$ and stirred under a $H_2$ atmosphere overnight (18 h). Then Pd/C was filtered off and solvent was evaporated to afford 0.42 g (quant.) product as amorphous solid.

$^1$H NMR (401 MHz, $CDCl_3$): $\delta_H$ 1.22 (dd, J=13.0, 6.3, 6H), 1.83-1.94 (m, 1H), 1.96 (s, 3H), 2.10-2.31 (m, 3H), 3.15-3.31 (m, 1H), 4.43-4.52 (m, 1H), 4.80-4.89 (m, 1H), 4.96 (p, J=6.3, 1H), 6.56 (d, J=8.0, 1H), 6.94 (d, J=7.7, 1H), 7.05-7.21 (m, 3H), 7.33 (d, J=8.2, 1H), 7.59 (d, J=7.9, 11H), 8.33 (s, 1H).

$^{13}$C NMR (101 MHz, $CDCl_3$): $\delta_C$ 21.7, 23.1, 26.9, 28.1, 30.0, 52.1, 54.1, 69.5, 110.0, 111.4, 118.4, 119.6, 122.0, 123.5, 127.6, 136.2, 170.7, 171.0, 171.9, 176.2.

Optical rotation: $[\alpha]^{22}_D$ −27.5° (c 0.258; DMF).

IR (KBr): 3473, 3406, 3290, 3061, 3000, 2618, 1730, 1716, 1652, 1534, 1458, 1437, 1386, 1375, 1290, 1267, 1256, 1218, 1105, 1075, 1011, 744 cm-1.

ESI MS: 440.2 ([M+Na]$^+$).

HR ESI MS: Calcd. for $C_{21}H_{27}O_6N_3Na$ 440.17921. Found: 440.17883.

EXAMPLE 7

Synthesis of Isopropyl (S)-2-((S)-acetamido-3-(1H-indol-3-yl)propanamido)-6-diazo-5-oxohexanoate (Compound 1a)

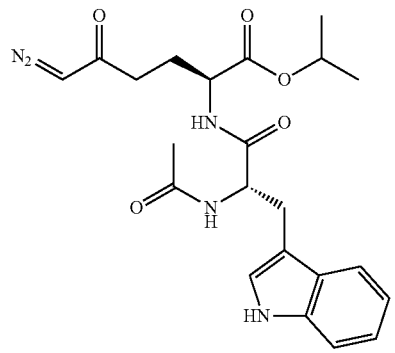

Compound 6a (0.1 g, 0.24 mmol) was dissolved in anhydrous tetrahydrofuran (5 mL) and isobutylchloroformate (62 uL, 0.48 mmol) and triethylamine (0.1 mL, 0.72 mmol) were added and the reaction mixture was stirred at −20° C. for 2.5 hours. A 0.5M solution of diazomethane in diethylether (2.5 mL) was added and the reaction mixture was stirred at −20° C. for 48 hours. The volatiles were then evaporated and the residue was re-dissolved with ethyl acetate (60 mL) and washed with saturated aqueous ammonium chloride (15 mL), and brine (15 mL). The organic portion was dried using anhydrous sodium sulphate. The volatiles were evaporated and residue was subjected to flash column chromatography (Silicagel 60 mesh 70-230, solvent: dichloromethane/methanol 30:1) to afford 81 mg (76%) of Compound 1a as white solid.

$^1$H and $^{13}$C NMR spectra were in agreement with the published data.

EXAMPLE 8

Synthesis of 5-(tert-butyl) 1-isopropyl ((benzyloxy)carbonyl)-L-glutamate (Compound A 1)

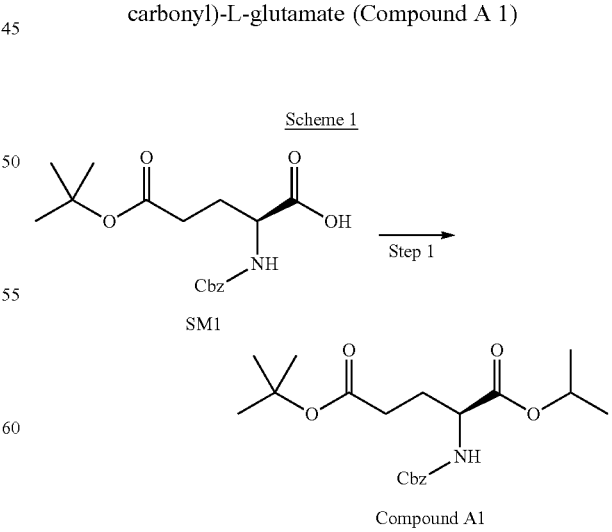

Scheme 1

Table 1.1 provides the starting materials and results of the chemical reaction described in Scheme 1. The reaction was carried out in two stages in DCM. CDI without any base maintained good to excellent ee, while adding bases lowered the ee. FIG. 1 shows the ee compound A1 from entry 2 of Table 1.1.

Table 1.2 provides the solvent effect of the chemical reaction described in Scheme 1. DCM is the best solvent to maintain high ee.

Table 1.3 provides the effect of different amounts of CDI for the chemical reaction described in Scheme 1. The amount of CDI can be reduced to about 1.3 equiv. High ee is maintained under these conditions.

Table 1.4 provides the reaction temperature effect of the chemical reaction described in Scheme 1. A reaction temperature at 0° C. is beneficial to maintain the high ee.

Table 1.5 provides the activator effect of the chemical reaction described in Scheme 1.

Table 1.6 provides the different activator effects of the chemical reaction described in Scheme 1.

In a representative process, into a 10 L reactor was added (S)-2-(benzyloxycarbonylamino)-5-tert-butoxy-5-oxopentanoic acid (600 g, 1.0 eq.) in DCM (6 L, 10 V) under $N_2$ protection with stirring. The reaction mixture was cooled to 0° C. To the reactor was added CDI (375 g, 1.3 eq.) batchwise while maintaining the temperature at 0-5° C. The resulting reaction mixture was allowed to stir for 3 h while maintaining the temperature at 0-5° C. Then propan-2-ol (534.4 g, 5.0 eq.) was added to the reaction mixture and allowed to stir overnight while maintaining the temperature at 0-5° C. To the reaction mixture was added water (1.8 L, 3 V). The reaction mixture was allowed to warm to 20° C. and stirred for 0.5 h. The phases were separated and the organic phase was collected. The organic phase was washed with water (3 V) and brine (3 V). The organic phase was concentrated under vacuum until the residue was no more than 1.2 L (2 V) left. The residue was switched with MTBE (1.8 L) two times under vacuum until the residue was no more than 1.2 L (2 V) left. To the residue was added MTBE (2.4 L, 4 V). The undissolving solid was filtered out and the filtrate was concentrated under vacuum until there was no solvent left. This resulted in about 726 g of crude light yellow oil with 93.8% HPLC purity. This material could be directly used in the next step. $^1$H NMR (400 MHz, DMSO): δ 7.71-7.69 (m, 1H), 7.37-7.30 (m, 5H), 5.05 (s, 1H), 4.91-4.87 (m, 11H), 4.04-3.99 (m, 1H), 2.31-2.28 (m, 2H), 1.93-1.76 (m, 2H), 1.41 (s, 9H), 1.21 (m, 6H).

EXAMPLE 9

Synthesis of 5-(tert-butyl) 1-isopropyl (((9H-fluoren-9-yl)methoxy)carbonyl)-L-glutamate (Compound A2)

Scheme 2

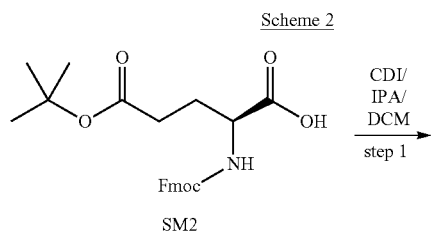

SM2

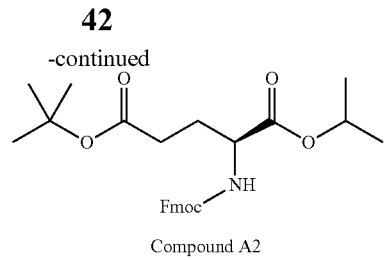

Compound A2

Table 2.1 provides the starting materials, reaction times, and results of the chemical reaction described in Scheme 2. The reactions were conducted in DCM.

EXAMPLE 10

Synthesis of 5-(tert-butyl) 1-isopropyl L-glutamate (Compound A3)

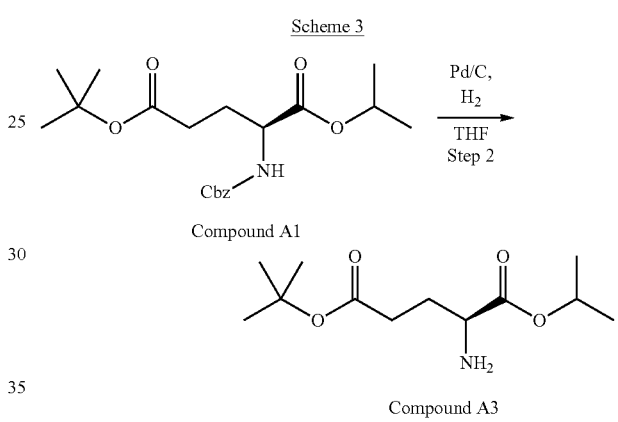

Table 3.1 provides the starting materials, reaction times, and results of the chemical reaction described in Scheme 3. The reactions were conducted in THF (15 V). The hydrogenation reaction can be conducted with a relatively low pressure of $H_2$.

EXAMPLE 11

Synthesis of 5-(tert-butyl) 1-isopropyl L-glutamate (Compound A3)

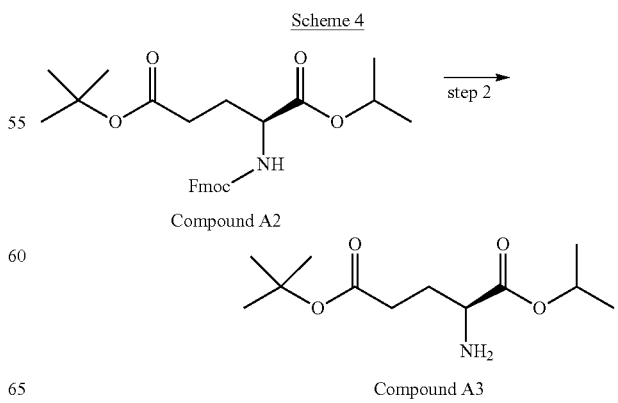

Table 4.1 provides the starting materials, reaction times, and results of the chemical reaction described in Scheme 4.

EXAMPLE 12

Formation of Salts of Compound A3

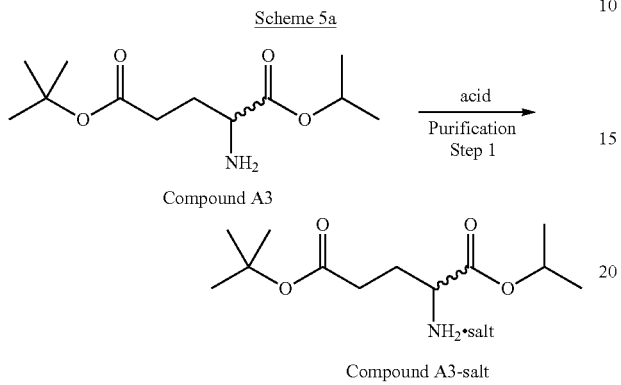

Scheme 5a
Compound A3
Compound A3-salt

Table 5.1 provides the raw material, solvent, and reagents of the purification process described in Scheme 5a. Compound A3 can treated with oxalic acid and L-tartaric acid to form a salt. Isolation of the Compound A3-salt and subsequent conversion back to the free-base form improves the chemical and/or chiral purity of Compound A3.

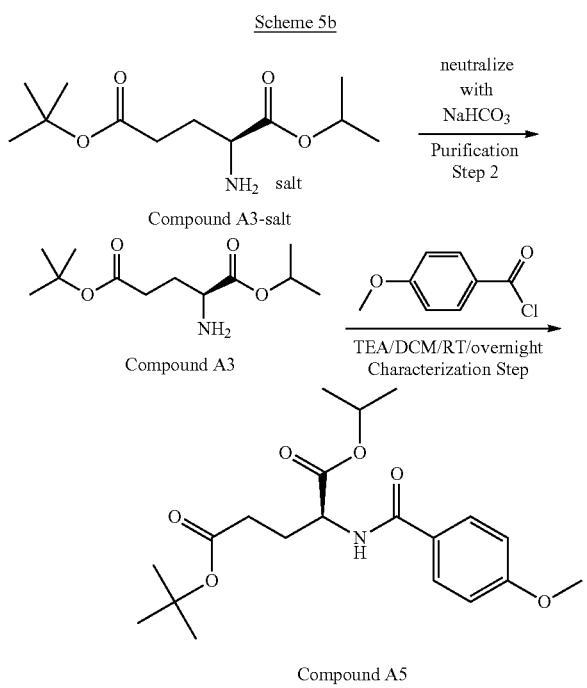

Scheme 5b
Compound A3-salt
Compound A3
Compound A5

The ee of Compound A3 was evaluated by chemical derivatization to give Compound A5 which was analyzed by chiral HPLC. See Table 5.2.

Figure 2A:
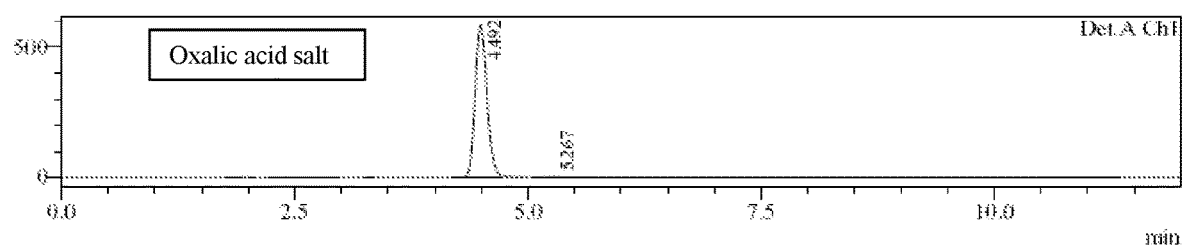
FIG. 2A is a chiral HPLC chromatogram showing the chiral resolution of Compound A5 when the acid used in Scheme 5a is oxalic acid.
Figure 2B:
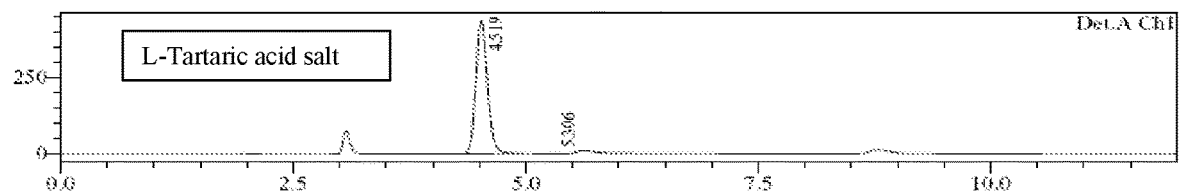
FIG. 2B is a chiral HPLC chromatogram showing the chiral resolution of Compound A5 when the acid used in Scheme 5a is L-tartaric acid.
Figure 2C:
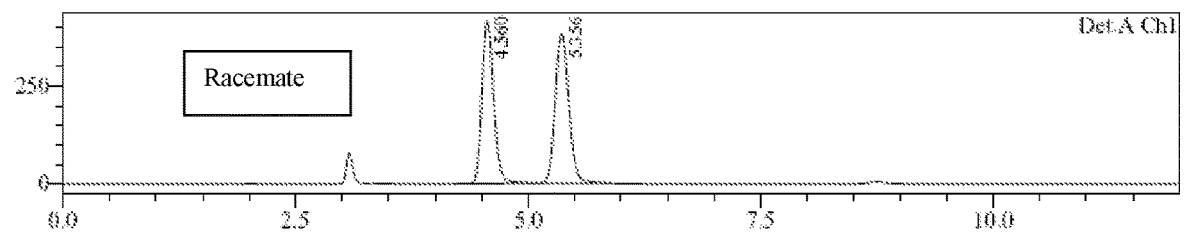
FIG. 2C is a chiral HPLC chromatographic showing the chiral resolution of racemic Compound A5.

The ee of the Compound A3 was improved through salt precipitation. FIGS. 2A-C provides chiral HPLC chromatograms showing chiral purity of Compound A5.

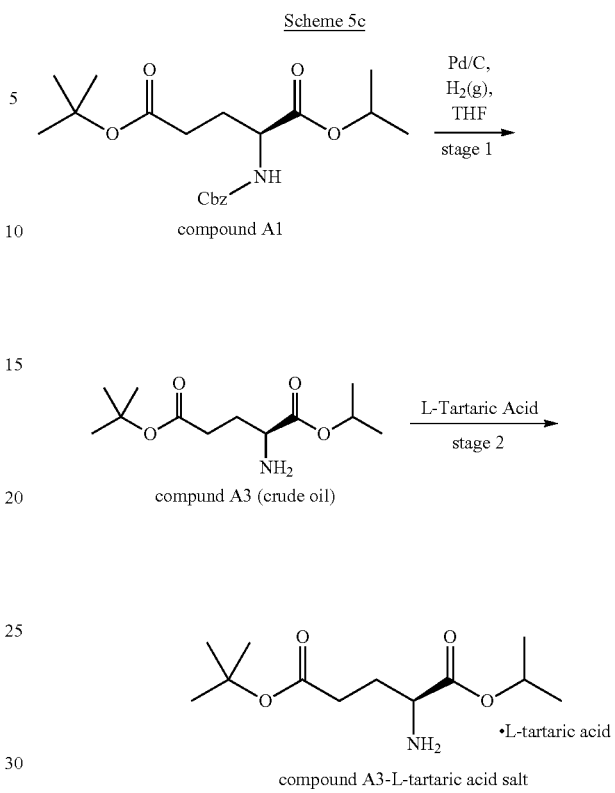

Scheme 5c
compound A1
compund A3 (crude oil)
compound A3-L-tartaric acid salt

Stage 1:

Into a 10 L reactor was added compound A1 (350 g, 1.0 eq.) and THF (5.3 L, 15 V) under $N_2$ protection protection with stirring. To the reactor was added 10% Pd/C (wet. (60% water content), 35 g, 0.1 w/w) under an atmosphere of $N_2$. The reaction mixture was placed under at atmosphere of $H_2$ and allowed to react at room temperature overnight while maintaining the system under an atmosphere of $H_2$ (1-2 atm.). This reaction was repeated two times at the same scale and the reaction mixtures were combined. A filtration was performed and the solid was washed with THF (3.5 L, 5 V). The filtrate was concentrated under vacuum until there was no solvent left. This resulting 540 g crude light yellow oil and used directly to form the compound A3 salt with L-tartaric acid.

Stage 2:

Into a 50 L reactor was added propan-2-ol (18.9 L, 35 V) and L-tartaric acid (267 g, 1.0 eq.) with stirring. To the mixture was added a mixture of the above crude oil (540 g) in propan-2-ol (2.7 L, 5 V) while maintaining the temperature at 15±5° C. over a period of 2.6 h. A white solid precipitated out gradually and the sticky slurry was allowed to stir for 2.5 h at 15±5° C. A filtration was performed and the solid was washed with propan-2-ol (2.7 L, 5 V). The white solid was collected and dried overnight under vacuum while maintaining the temperature at 35~40° C. Compound A3-L-tartaric acid (565 g) was obtained as a white solid with 100% chemical purity (as determined by HPLC) and >99% chiral purity (as determined by chiral HPLC after derivatization with 4-methoxybenzoyl chloride). $^1$H NMR (400 MHz, DMSO): δ 7.06 (s, 6H), 4.98-4.95 (m, 1H), 4.05 (s, 2H), 3.76-3.73 (m, 1H), 2.40-2.29 (m, 2H), 2.31-2.28 (m, 2H), 1.93-1.82 (m, 2H), 1.41 (s, 9H), 1.21 (m, 6H).

EXAMPLE 13

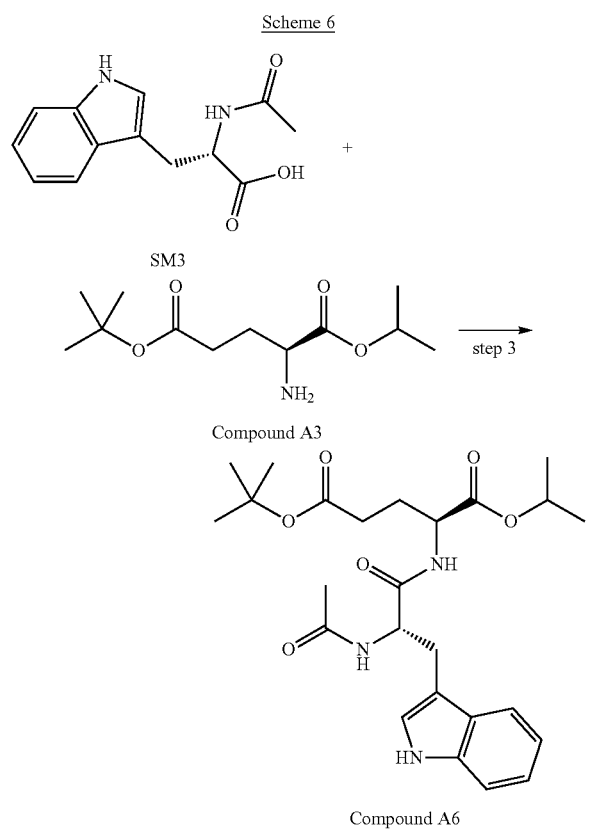

Figure 3A:
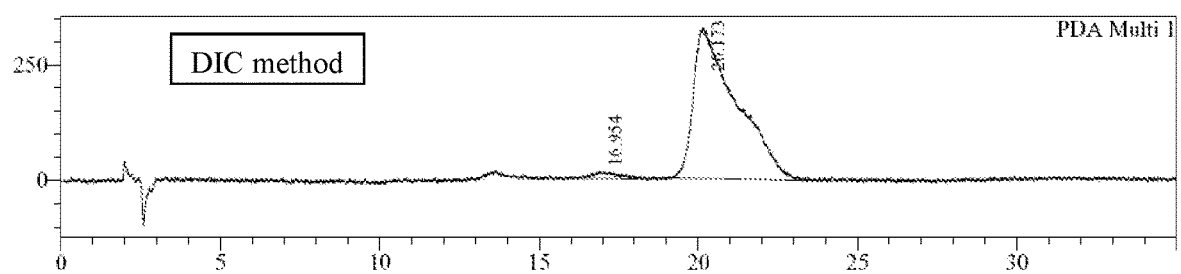
FIG. 3A is a chiral HPLC chromatogram showing the ee of compound A6 when the coupling agent used in Scheme 6 comprise OxymaPure®, DIC, and 2,4,6-collidine.
Figure 3B:
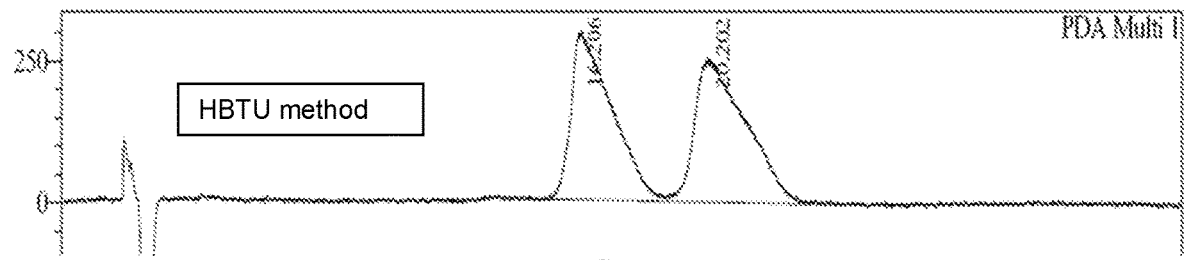
FIG. 3B is a chiral HPLC chromatogram showing the ee of compound A6 when the coupling reagent used in Scheme 6 comprises HBTU and DIEA.

Table 6.1 provides the starting materials, solvent, and results of the chemical reaction described in Scheme 6. When the coupling agent comprises diisopropylcarbodiimide as the activator, 2,4,6-collidine as the base, and OxymaPure® as the additive, minimal stereomutations is obseved to give the desired production in high ee. FIGS. 3A and 3B provide chiral HPLC chromatograms showing the ee of the Compound A6.

EXAMPLE 13A

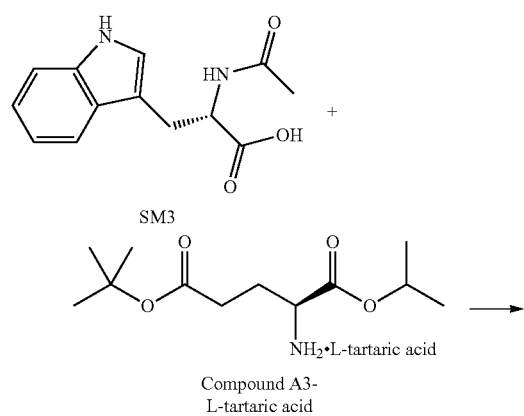

Stage 1:
Into a 5 L reactor compound A3-L-tartaric acid (372 g, 1.0 eq.) was dissolved in water (1.9 L, 5 V) with stirring. The pH of the solution was adjusted to ~8 with sat. $NaHCO_3$ solution. The mixture was extracted with DCM (10 V*3). The organic phases were combined together and concentrated under vacuum until there was no solvent distilled out. This resulting 214 g of free base (compound A3) was obtained as a light yellow oil. Another batch containing 206 g free base was obtained from 360 g of compound A3-L-tartaric acid.

Stage 2:
Into a 10 L reactor was added a mixture of N-acetyl-L-tryptophan (SM3) (180 g, 1.0 eq.) in DCM (3.6 L, 20 V). The mixture was cooled to 0-10° C. To this was added OxymaPure® (103.3 g, 1.0 eq.) and 2,4,6-collidine (114.5 g, 1.3 eq.) and a solution of 214 g the above free base in DCM (0.9 L, 5 V). To the above reaction mixture was finally added EDC.HCl (139.3 g, 1.0 eq.). The reaction mixture was allowed to stir overnight at 20±5° C. Another portion of EDC.HCl (27.9 g, 0.2 eq.) was added to the mixture and the reaction mixture was allowed to stir for 2 h at 20±5° C. The reaction mixture was washed with water (5 V*3) and the organic phase was concentrated under vacuum. The resulted in 614 g of crude product as a sticky oil. Another batch containing 433 g crude sticky oil was obtained from 130 g N-acetyl-L-tryptophan. The two batches of crude oil were combined together and purified by column chromatography using EtOAc/PE as eluate (1:10 to 3:2). Total 519 g light yellow oil was obtained after purification with high HPLC purity. $^1H$ NMR (400 MHz, DMSO): δ 10.80 (s, 1H), 8.43-8.41 (d, 1H), 8.05-8.03 (m, 1H), 7.62 (d, 1H), 7.33-7.31 (d, 1H), 7.15 (d, 1H), 7.08-6.96 (m, 2H), 4.92-4.89 (m, 1H), 4.58 (m, 1H), 4.23 (m, 1H), 3.12-3.08 (m, 1H), 2.91-2.84 (m, 11H), 2.30-2.25 (m. 1H), 1.96 (m, 1H), 1.82-1.76 (m, 4H), 1.41 (s, 9H), 1.21 (m, 6H).

EXAMPLE 14

Scheme 7

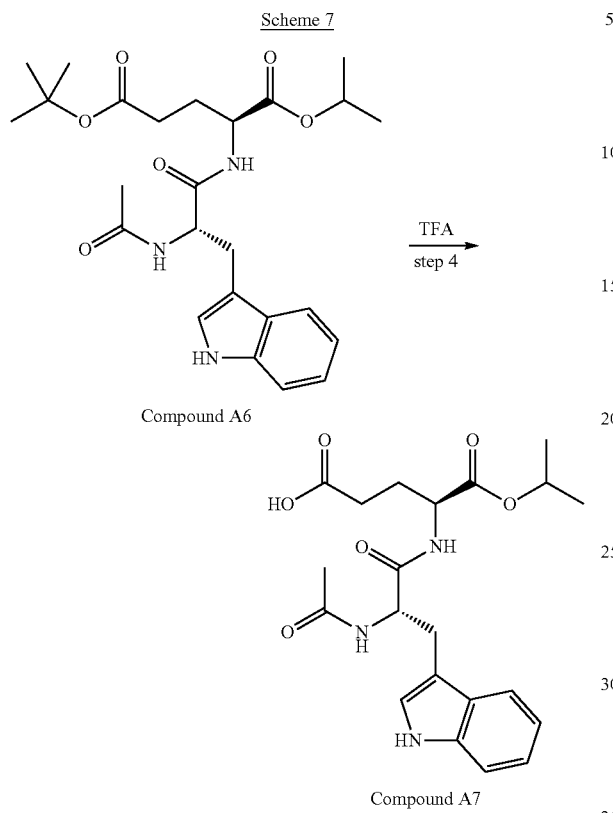

Compound A6

Compound A7

Table 7 provides the starting materials, solvent, and results of the chemical reaction described in Scheme 7. No racemization of Compound A6 occurred in the deprotection step (data not shown). Other conditions such as 4M HCl in isopropyl alcohol and 4 N HCl in 1,4-dioxane gave lower yields of compound A7 and more undesired by-products.

In a representative process, Compound A6 (220 g, 1.0 eq.) in DCM (2.2 L, 10 V) was added into a 10 L reactor with stirring under $N_2$ protection. The reaction mixture was cooled to 15° C. with an ice/water bath. To the reactor was added dropwise TFA (484 mL, 2.2 V) while maintaining the temperature at 10-20° C. The resulting reaction mixture was allowed to stir for 5 h while maintaining the temperature at 15-25° C. The reaction mixture was concentrated under vacuum until there was no solvent left to be distilled out and then switched with DCM (5 V*3) and then switched with MTBE (5 V*3) until the residue was no more than 5 V (1.1 L) left. The slurry was allowed to stir overnight at 15~25° C. A filtration was performed and the solid was collected. The solid was combined with another batch from 50 g of Compound A6 and re-slurried with ACN (3 V/solid) at 15~25° C. A filtration was performed and the solid was collected and dried under vacuum at 20-25° C. This resulted 148.8 g of Compound A7 as a pale pink solid with 97.8% HPLC purity. Crude yield: 62%. $^1$H NMR (400 MHz, DMSO): δ 12.20 (s, 1H), 10.80 (s, 1H), 8.43-8.41 (d, 1H), 8.05-8.03 (m, 1H), 7.63-7.62 (d, 1H), 7.33-7.31 (d, 1H), 7.15 (d, 1H), 7.08-6.96 (m, 2H), 4.92-4.89 (m, 1H), 4.58 (m, 1H), 4.23 (m, 1H), 3.12-3.08 (m, 1H), 2.91-2.84 (m, 11H), 2.30-2.25 (m. 2H), 1.96 (m, 1H), 1.82-1.76 (m, 4H), 1.21 (m, 6H).

EXAMPLE 15

Synthesis of isopropyl (S)-2-((S)-2-acetamido-3-(1H-indol-3-yl)propanamido)-6-diazo-5-oxohexanoate

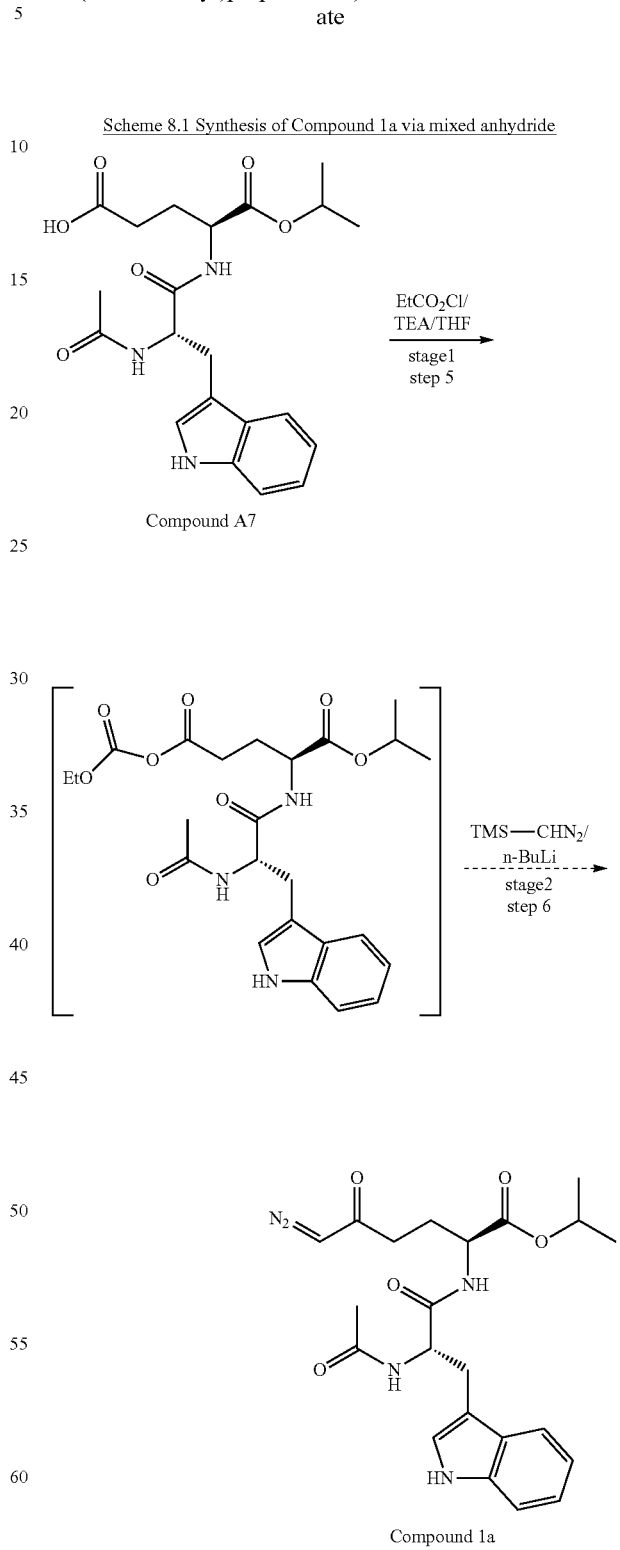

Scheme 8.1 Synthesis of Compound 1a via mixed anhydride

Compound A7

Compound 1a

Table 8.1 provides the starting materials, solvent, and results of the chemical reaction described in Scheme 8.1. This reaction failed to give Compound 1a.

Scheme 8.2 Synthesis of the Compound 1a via acyl chloride

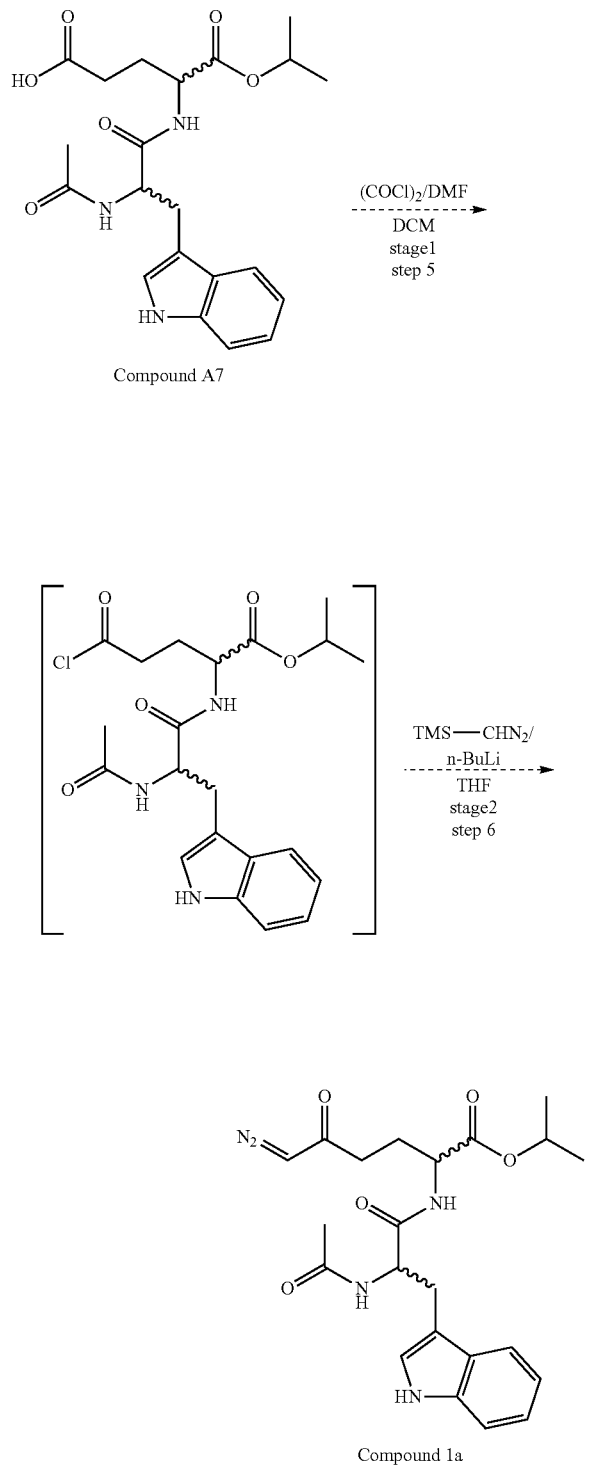

Scheme 8.3 Synthesis of the Compound 1a via methanesulfonate

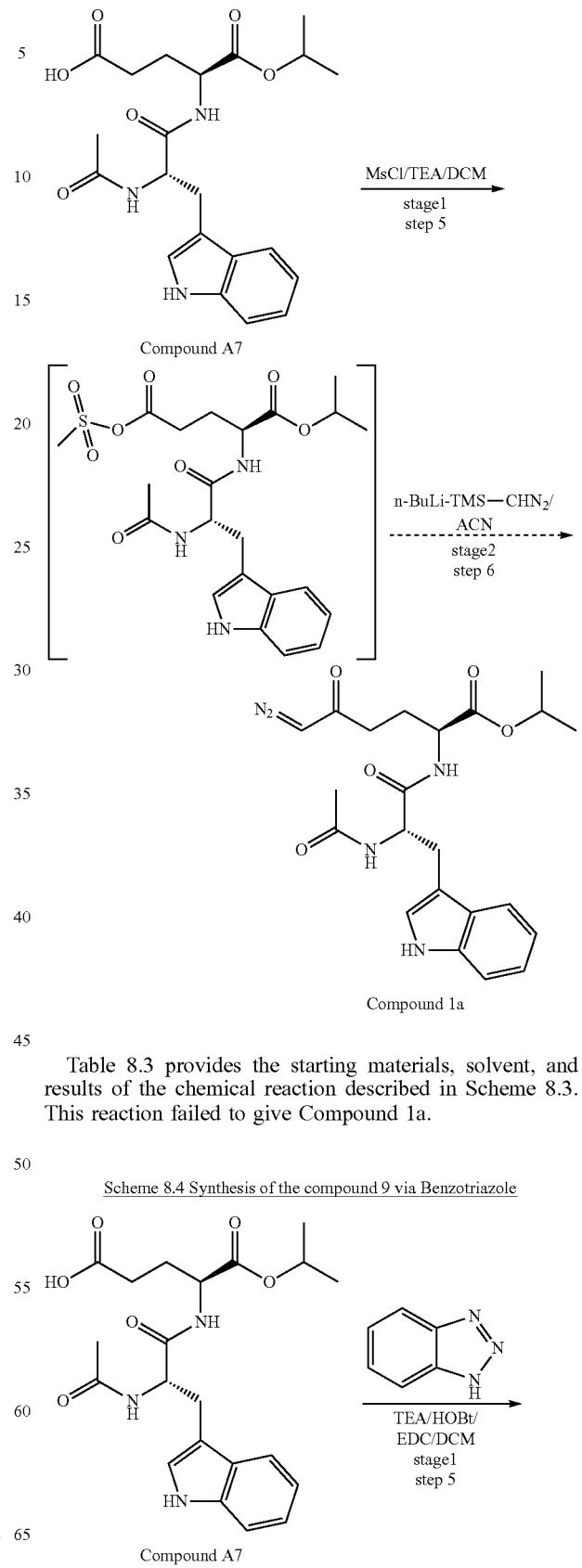

Table 8.3 provides the starting materials, solvent, and results of the chemical reaction described in Scheme 8.3. This reaction failed to give Compound 1a.

Scheme 8.4 Synthesis of the compound 9 via Benzotriazole

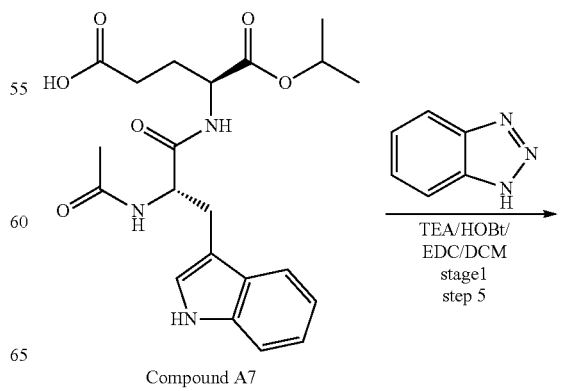

Table 8.2 provides the starting materials, solvent, and results of the chemical reaction described in Scheme 8.2. This reaction failed to give Compound 1a.

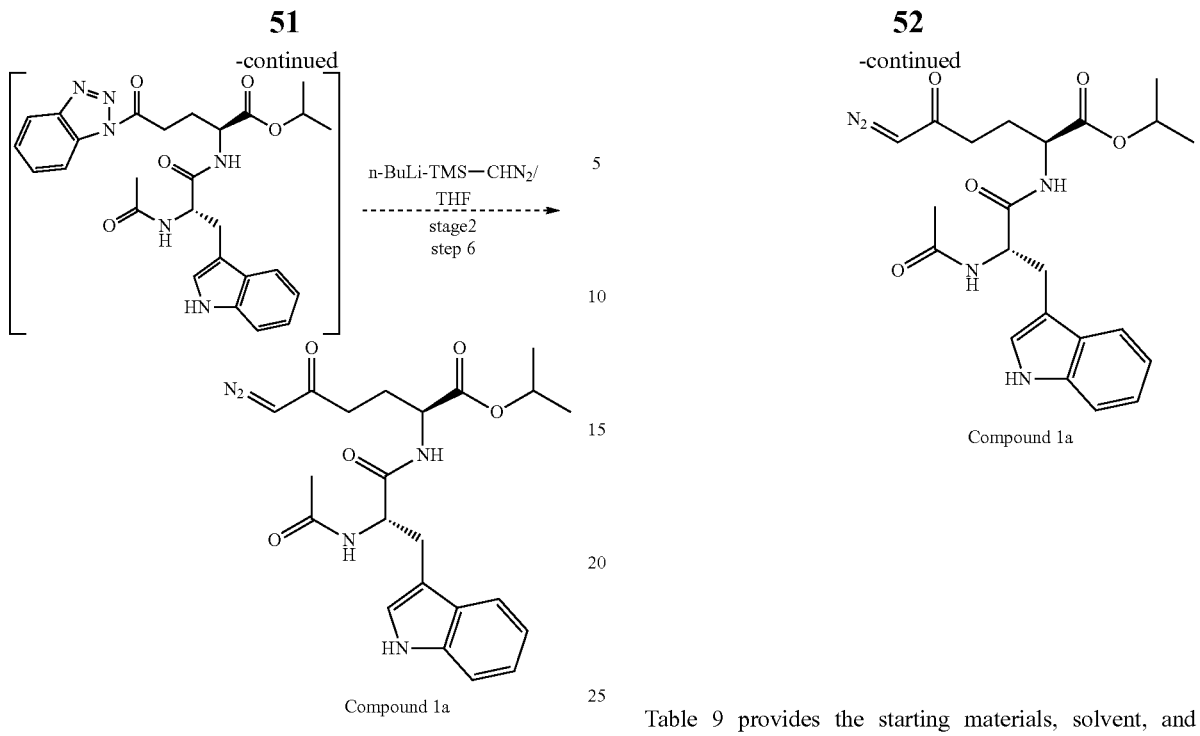

Compound 1a

Table 8.4 provides the starting materials, solvent, and results of the chemical reaction described in Scheme 8.4. This reaction failed to give Compound 1a.

EXAMPLE 16

Scheme 9 Synthesis of the Compound 1a via Diazomethane

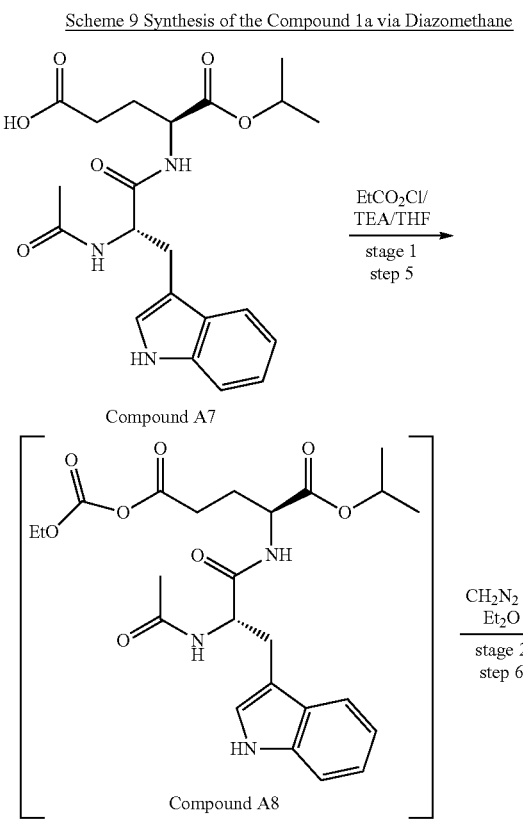

Figure 4:
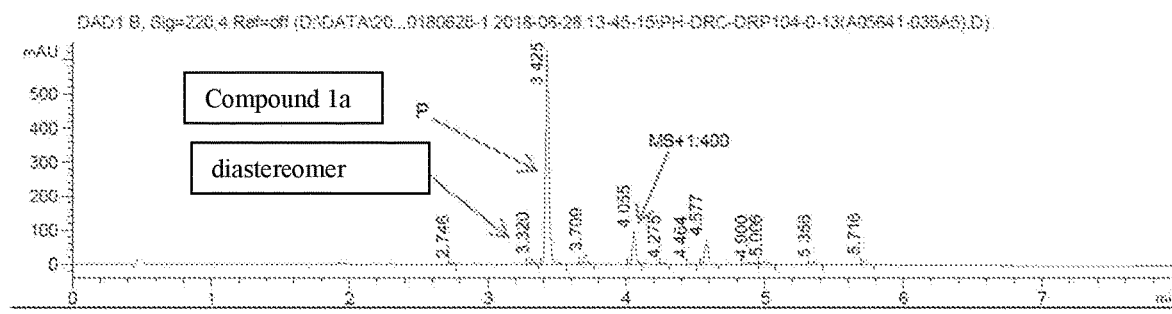
FIG. 4 is a LCMS chromatogram showing the chemical purity of crude compound 1a obtained by the synthetic scheme described in Example 16.

Table 9 provides the starting materials, solvent, and results of the chemical reaction described in Scheme 9. Diazomethane reacted with the mixed anhydride intermediate (Compoound A8) to afford Compound 1a. FIG. 4 provides a HPLC chromatogram showing about 70% of Compound 1a was generated in the reaction.

In a representative process, Compound A7 (3.0 g, 1.0 eq.) in THF (60 mL, 20 V) was added into a 250 mL reactor under $N_2$ protection. The reaction mixture was cooled to below −30° C. TEA (0.76 g, 1.05 eq.) was added to the reaction mixture. To the above reactor was added dropwise ethyl carbonochloridate (0.82 g, 1.05 eq.) while maintaining the temperature at −30~−20° C. The resulting reaction mixture was allowed to stir for 2 h while maintaining the temperature at −30 to −20° C. To the reaction mixture was added dropwise $CH_2N_2$ in $Et_2O$ (0.3 M, 5.0 eq.) while maintaining the temperature below 0° C. Then the reaction mixture was allowed to stir overnight at 0-10° C. To the reaction mixture was added water (7 V) and the mixture was allowed to stir for 10 min. The phases were separated and the aqueous phase was extracted with DCM (10 V). The organic phases were combined together and concentrated under vacuum. The obtained residue was purified by column chromatography using DCM/MeOH (75:1) as eluent. The eluent was concentrated under vacuum and the residue was slurried with EtOAc (5 V/solid). A filtration was performed and the solid was collected and dried under vacuum at 20-25° C. This resulted 500 mg of product as a light yellow solid with 98.9% HPLC purity. Yield: 15.6%. $^1$H-NMR (400 MHz, DMSO): δ 10.80 (s, 1H), 8.43-8.41 (d, 1H), 8.05-8.03 (m, 1H), 7.63-7.61 (d, 1H), 7.33-7.31 (d, 1H), 7.15 (d, 1H), 7.08-6.96 (m, 2H), 6.02 (s, 1H), 4.94-4.85 (m, 1H), 4.59-4.53 (m, 1H), 4.22-4.15 (m, 1H), 3.12-3.06 (m, 1H), 2.91-2.83 (m, 1H), 2.44-2.38 (m. 2H), 1.96 (m, 1H), 1.82-1.76 (m, 4H), 1.19-1.16 (m, 6H).

TABLE 1.1

Esterification with CDI

| | | Stage 1 | | | | Stage 2 | | | |
|---|---|---|---|---|---|---|---|---|---|
| | Starting Materials 1 | | | Reaction Conditions 1 | | Starting Materials 2 | Reaction Conditions 2 | | |
| Entry | SM1 | CDI | Base | Temp (° C.) | Time (h) | i-PrOH | Temp (° C.) | Time (h) | Result |
| 1 | 400.0 g (1.0 eq.) | 1.3 eq. + 0.08 eq. | N/A | 0-5 | 3 h + 1 h | 5.0 eq. | 0-5 | 12 h | 540 g crude light yellow oil obtained, HPLC purity: 93.8%; Chiral purity: 98.22% |
| 2 | 20.0 g (1.0 eq.) L-Form | 2.0 eq. | N/A | 15 ± 5 | 1.5 h | 5.0 eq. | 20 ± 5 | overnight | 20.3 g light yellow oil obtained purification by column, HPLC purity: 99%; Chiral purity: 96.85% |
| 3 | 10.0 g (1.0 eq.) Enantiomer | 2.0 eq. | N/A | 15 ± 5 | 1.5 h | 5.0 eq. | 20 ± 5 | overnight | 6.3 g light yellow oil obtained purification by column, HPLC purity: 99%; Chiral purity: 96.81% |
| 4 | 2.0 g (1.0 eq.) | 2.0 eq. | TEA (1.1 eq.) | 15 ± 5 | 3 | 5.0 eq. | 25 ± 5 | 15 | 2.0 g crude light brown oil, Chiral purity: 83.81%. |
| 5 | 2.0 g (1.0 eq.) | 2.0 eq. | DIEA (1.1 eq.) | 15 ± 5 | 3 | 5.0 eq. | 25 ± 5 | 15 | 2.1 g crude light brown oil, Chiral purity: 86.89% |
| 6 | 2.0 g (1.0 eq.) | 2.0 eq. | NMM (1.1 eq.) | 15 ± 5 | 3 | 5.0 eq. | 25 ± 5 | 15 | 2.2 g crude light yellow oil, Chiral purity: 91.98% |
| 7 | 10.0 g (1.0 eq.) | 2.0 eq. | N/A | 15-20 | 2 | 5.0 eq. | 20-25 | 15 | ~15 g crude yellow oil |
| 8 | 300.0 g (1.0 eq.) | 2.0 eq. | N/A | 15-20 | 1 | 5.0 eq. | 20-25 | 17 | ~500 g crude yellow oil |
| 9 | 50.0 g (1.0 eq.) D-Form | 2.0 eq. | N/A | 15-20 | 1 | 5.0 eq. | 20-25 | 16.5 | ~86 g crude light yellow oil |
| 10 | 50.0 g (1.0 eq.) L-Form | 2.0 eq. | N/A | 15-20 | 4 | 5.0 eq. | 20-25 | 16.5 | ~85 g crude light yellow oil |
| 11 | 400.0 g (10 eq) | 1.3 eq. | N/A | 0-5 | 3 h | 5.0 eq. | 0-5 | 15 | 726 g crude light yellow oil obtained, HPLC purity: 93.8% |

TABLE 1.2

Solvent Effect

| | | Stage 1 | | | | Stage 2 | | | |
|---|---|---|---|---|---|---|---|---|---|
| | Starting Materials 1 | | | Reaction Conditions 1 | | Starting Materials 2 | Reaction Conditions 2 | | |
| Entry | SM1 | CDI | Solvent | Temp (° C.) | Time (h) | i-PrOH | Temp (° C.) | Time (h) | Result |
| 1 | 20.0 g (1.0 eq.) | 2.0 eq. | DCM (10 V) | 15 ± 5 | 1.5 | 5.0 eq. | 25 ± 5 | overnight | 20.3 g light yellow oil obtained purification by column, HPLC purity: 99%; Chiral purity: 96.85% |
| 2 | 2.0 g (1.0 eq.) | 2.0 eq. | CAN (10 V) | 15 ± 5 | 1.5 | 5.0 eq. | 25 ± 5 | 28 | 2.2 g crude colorless oil, Chiral purity: 94.09% |
| 3 | 2.0 g (1.0 eq.) | 2.0 eq. | THF (10 V) | 15 ± 5 | 1.5 | 5.0 eq. | 25 ± 5 | 28 | 2.1 g crude colorless oil, Chiral purity: 90.75% |
| 4 | 2.0 g (1.0 eq.) | 2.0 eq. | DMF (10 V) | 15 ± 5 | 1.5 | 5.0 eq. | 25 ± 5 | 43.5 | 2.1 g crude colorless oil, Chiral purity: 90.75% |

TABLE 1.3

Different Equivalents of CDI

| | Stage 1 | | | | | Stage 2 | | | |
|---|---|---|---|---|---|---|---|---|---|
| | Starting Materials1 | | | Reaction Conditions 1 | | Starting Materials 2 | Reaction Conditions 2 | | |
| Entry | SM1 | CDI | Solv. | Temp (° C.) | Time (h) | i-PrOH | Temp (° C.) | Time (h) | Result |
| 1 | 20.0 g (1.0 eq.) | 2.0 eq. | DCM (10 V) | 15 ± 5 | 1.5 | 5.0 eq. | 25 ± 5 | overnight | 20.3 g light yellow oil obtained purification by column, HPLC purity: 99%; Chiral purity: 96.85% |
| 2 | 2.0 g (1.0 eq.) | 1.1 eq. + 0.1 eq. | DCM (10 V) | 15 ± 5 | 1.5 + 1 | N/A | N/A | N/A | 10% SM left (1.1 eq. CDI); 3.3% SM left (1.2 eq. CDI) |
| 3 | 2.0 g (1.0 eq.) | 1.3 eq. | DCM (10 V) | 15 ± 5 | 1.5 | N/A | N/A | N/A | 0.4% SM left |
| 4 | 30.0 g (1.0 eq.) | 1.3 eq. | DCM (10 V) | 15 ± 5 | 1.5 | 5.0 eq. | 25 ± 5 | 14.5 | 36.5 g crude light yellow oil without any purification Chiral purity: 96.1% |

TABLE 1.4

Reaction Temperature

| | Stage 1 | | | | | Stage 2 | | | |
|---|---|---|---|---|---|---|---|---|---|
| | Starting Materials 1 | | | Reaction Conditions 1 | | Starting Materials 2 | Reaction Conditions 2 | | |
| Entry | SM1 | CDI | Solv. | Temp (° C.) | Time (h) | i-PrOH | Temp (° C.) | Time (h) | Result |
| 1 | 20.0 g (1.0 eq.) | 2.0 eq. | DCM (10 V) | 15 ± 5 | 1.5 | 5.0 eq. | 25 ± 5 | overnight | 20.3 g light yellow oil obtained purification by column, HPLC purity: 99%; Chiral purity: 96.85% |
| 2 | 30.0 g (1.0 eq.) | 1.3 eq. + 0.05 eq. | DCM (10 V) | 0 | 5 | 5.0 eq. | 0 | 14.5 | 35.6 g crude light yellow oil without any purification Chiral purity: 99.15% |
| 3 | 20.0 g (1.0 eq.) Enantiomer | 1.3 eq. + 0.02 eq. | DCM (10 V) | 0 | 5 | 5.0 eq. | 0 | 14.5 | 21.5 g crude light yellow oil without any purification, Chiral purity: 99.13% |

TABLE 1.5

Activators I

| | Starting Materials | | | | Reaction Conditions | | |
|---|---|---|---|---|---|---|---|
| Entry | SM1 | HOBT | EDC•HCl | IPA | DMF | Temp (° C.) | Time (h) | Result |
| 1 | 40.0 g (1.0 eq.) | 2.25 eq. | 2.30 eq. | 10.0 eq. | 8 V | 20-25 | overnight | Work complex, prolong time no obvious progress. |
| 2 | 20 g (1.0 eq.) Enantiomer | 2.25 eq. | 2.30 eq. | 10.0 eq. | 8 V | 20-25 | overnight | Work complex, prolong time no obvious progress. |

TABLE 1.6

Activators II

| | Starting Materials | | | Reaction Conditions | | |
|---|---|---|---|---|---|---|
| Entry | SM1 | P-TsOH | solvent | Temp (° C.) | Time (h) | Results |
| 1 | 5 g (1.0 eq.) | 0.1 eq. | IPA (5 V) | 0-10 | 2 | No reaction |
| | | | | 20-30 | 2 | Trace product detected |
| | | | | 35-40 | 16 | 76.4% SM left, P: 20.9% |
| | | | | 40-45 | 24 | 50.5% SM left, P: 40.6%, 1.6% ester exchange by-product |
| 2 | 5 g (1.0 eq.) Enantiomer | 0.1 eq. | IPA (5 V) | 0-10 | 2 | No reaction |
| | | | | 20-30 | 2 | Trace product detected |
| | | | | 35-40 | 16 | 73.9% SM left, P: 21.8% |
| | | | | 40-45 | 24 | 48.5% SM left, P: 41.7%, 2.0% ester exchange by-product |

TABLE 1.7

Activator III

| | Starting Materials | | | | Reaction Conditions | | |
|---|---|---|---|---|---|---|---|
| Entry | SM | catalyst | Triisopropyl Orthoformate | Solv. | Temp (° C.) | Time (h) | Result |
| 1 | 20 g (1.0 eq.) | Amberlyst-15 ion exchange resin (10% w/w) | 1.2 eq. + 0.6 eq. | IPA (5 V) | 5~65 | 2~16 | No reaction |
| | | | | | 75~80 | 48 h | ~11% product detected |
| | | | | | 80~85 (reflux) | 4 | ~12% product detected |
| | | | | | | overnight | Too complex |
| 2 | 2 g (1.0 eq.) | Conc. H2SO4 (3% w/w) | 3.0 eq. | IPA (5 V) | 0~10 | 2 | No reaction |
| | | | | | 20~30 | 2 | ~1.3% product detected |
| | | | | | 35~40 | 3 | No progress |
| | | | | | 55~65 | 16 | No progress |
| | | | | | 75-80 | 5 | No progress |
| | | | | | 80~85 (reflux) | overnight | No SM left, but mainly ester exchange by-product was observed |

TABLE 2.1

| | Stage 1 | | | | Stage 2 | | | |
|---|---|---|---|---|---|---|---|---|
| | Starting Materials 1 | | Reaction Conditions 1 | | Starting | Reaction Conditions 2 | | |
| Entry | SM1 (KF: 3.9%) | CDI (eq.) | Temp (° C.) | Time (h) | Materials 2 i-PrOH | Temp (° C.) | Time (h) | Result |
| 1 | 3.0 g (1.0 eq.) | 1.5 | 15-20 | 2 | N/A | N/A | N/A | N/A |
| 2 | 3.0 g (1.0 eq.) | 1.7 | 15-20 | 2 | N/A | N/A | N/A | N/A |
| 3 | 3.0 g (1.0 eq.) | 2.0 | 15-20 | 2 | 5.0 eq. | 20-25 | 3.5 | Less than 1% INT left. Telescope (without work-up) |
| 4 | 30.0 g (1.0 eq.) | 2.0 | 15-20 | 1.5 | 5.0 eq. | 20-25 | 15 | Less than 1% INT left. Telescope (without work-up) |
| 5 | 300.0 g (1.0 eq.) | 2.0 | 15-20 | 1 | 5.0 eq. | 20-25 | 15 | Less than 1% INT left. Telescope (without work-up) |

TABLE 3.1

| | Starting Materials | | | Reaction Conditions | | |
|---|---|---|---|---|---|---|
| Entry | Compound A1 | Pd/C (wet.) | H₂ | Temp. (° C.) | Time (h) | Result |
| 1 | 5 g | 10% w/w | 1~2 atm. | RT | 3.5 h | 3.2 g light yellow oil HNMR-assay: 93.05%, yield: 93% |
| 2 | 2 g Enantiomer | 10% w/w | 1~2 atm. | RT | 3.5 h | 1.4 g light yellow oil HNMR-assay: 101.30%, yield >100% |
| 3 | 12 g | 10% w/w | 1~2 atm. | RT | 3.5 h | 7.7 g light yellow oil |
| 4 | 6 g (crude) Chiral purity: 96.1% | 10% w/w | 1~2 atm. | RT | overnight | 3.6 g crude gray oil |
| 5 | 30 g (crude) Chiral purity: 96.1% | 10% w/w | 1~2 atm. | RT | 5 h | 20.2 g crude gray oil |
| 6 | 20 g (crude) Chiral purity: 99.15% | 10% w/w | 1~2 atm. | RT | 4 h | 12.5 g crude light yellow oil |
| 7 | 10 g (crude Enantiomer) Chiral purity: 99.13% | 10% w/w | 1~2 atm. | RT | 4 h | 6.1 g crude light yellow oil |
| 8 | 1 g | 20% w/w | 8 atm. | 20-30 | 19 | 7.5 g light brown oil, HNMR assay: 69.46%, yield: 80% over 2 steps |
| 9 | 13 g | 10% w/w | 8 atm. | 20-30 | 19 | |
| 10 | 250 g × 2 | 5% w/w | 8 atm. | 20-30 | 19 | 380 g light brown oil |
| 11 | 10 g (1.0 eq.) | 10% w/w | 1~2 atm. | RT | overnight | 7 g crude light yellow oil obtained |
| 12 | 260 g (1.0 eq.) | 10% w/w | 1~2 atm. | RT | overnight | 182 g crude light yellow oil obtained |
| 13 | 260 g (1.0 eq.) | 10% w/w | 1~2 atm. | RT | overnight | 185 g crude light yellow oil obtained |

TABLE 4.1

| | Starting Materials | | Reaction Conditions | | |
|---|---|---|---|---|---|
| Entry | Compound A2 | TEA | Temp (° C.) | Time (h) | Result |
| 1 | Telescope from example 2, entry 4 | 2 V | 25-35 | 40 | 30 g yellow gelatinous oil |
| 2 | Telescope from example 2, entry5 | 2 V | 25-35 | 49 | 320 g yellow semi-solid HNMR-assay: 44.37% yield: 81% over 2 steps |

TABLE 5.1

| Compound A3 | acid | solvent | Temp. (° C.) | Time (h) | Solid precipitation |
|---|---|---|---|---|---|
| 0.2 g | citric acid (0.5 eq.) | IPA (1 mL, 5 V) | 20-30 | overnight | No solid precipitated |
| | Oxalic acid (1.0 eq.) | IPA (2 mL, 10 V) | 20-30 | overnight | white solid precipitated |
| | P-TsOH (1.0 eq.) | IPA (1 mL, 5 V) | 20-30 | overnight | No solid precipitated |
| | L-Lactic acid (1.0 eq.) | IPA (1 mL, 5 V) | 20-30 | overnight | No solid precipitated |
| | L-Tartaric Acid (1.0 eq.) | IPA (5 mL, 25 V) | 20-30 | overnight | white solid precipitated |
| | L-(+)-Mandelic acid (1.0 eq.) | IPA (1 mL, 5 V) | 20-30 | overnight | No solid precipitated |

TABLE 5.1-continued

| Compound A3 | acid | solvent | Temp. (° C.) | Time (h) | Solid precipitation |
|---|---|---|---|---|---|
| 2 g Chiral purity: 96.1% | Oxalic acid (1.0 eq.) | IPA (20 mL, 10 V) | 20-30 | overnight | 2.1 g white solid was obtained, HNMR is OK, Chiral purity: 98.40% |
| | L-Tartaric Acid (1.0 eq.) | IPA (50 mL, 25 V) | 20-30 | overnight | 2.4 g white solid was obtained, HNMR is OK, Chiral purity: 98.75% |
| 15 g Chiral purity: 99.15% | Oxalic acid (1.0 eq.) | IPA (15 mL, 10 V) | 20-30 | 2 | 1.7 g white solid was obtained Chiral purity: 99.45% |
| | L-Tartaric Acid (1.0 eq.) | IPA (60 mL, 40 V) | 20-30 | 2 | 1.8 g white solid was obtained Chiral purity: 99.69% |
| 360 g crude oil | L-Tartaric Acid (1.0 eq.) | IPA (40 V) | 15-25 | 3 | 365 g white solid (salt) obtained, HPLC purity: 100% Chiral purity (by deriving): 99.72% |

TABLE 5.2

| Crude compound A3 | acid | compound 4 Step 1 product | Step 2 SM. | Purified Compound 3 Step 2 product | Char step | Compound A5 |
|---|---|---|---|---|---|---|
| 2 g chiral purity: 96% | oxalic acid | 2.1 g | 1 g | 0.6 g free base | 0.2 g | 0.22 g waxy solid, chiral purity: 98.40% |
| 2 g chiral purity: 96% | L-Tartaric Acid | 2.4 g | 12 g | 0.7 g free base | 0.2 g | 0.23 g waxy solid, chiralpurity: 98.75% |
| 15 g chiral purity: 99.15% | oxalic acid | 1.7 g | 1 g | 0.6 g free base | 0.2 g | 0.16 g waxy solid, chiralpurity: 99.45% |
| 15 g chiral purity: 99.15% | L-Tartaric Acid | 1.8 g | 12 g | 0.5 g free base | 0.2 g | 0.22 g waxy solid, chiralpurity: 99.69% |

TABLE 6.1

| | Starting Materials | | | | | Reaction Conditions | | |
|---|---|---|---|---|---|---|---|---|
| Entry | SM3 | Cmpd A3 | Activator | Base/additive | Solv. | Temp (° C.) | Time (h) | Result |
| 1 | 3.5 g 1.0 eq. | 1.5 eq. | HBTU 2.0 eq. | DIEA 3.0 eq. | NMP 10 V | 25-35 | 16 | ~4.9 g off-white solid with high purity (complete racemization) |
| 2 | 2.46 g 1.0 eq. L-Form | 1.20 eq. L-Form | DIC 1.0 eq. | OxymaPure ® (1.00 eq) + 2,4,6-collidine (1.3 eq.) | DCM 25 V | 20-25 | 16 | 3.6 g yellow semi-solid with 99.85% purity, trace isomer detected |
| 3 | 1.0 g 1.0 eq. L-Form | 1.20 eq. Enant. | DIC 1.0 eq. | OxymaPure ® (1.00 eq) + 2,4,6-collidine (1.3 eq.) | DCM 25 V | 20-25 | 16 | 1.8 g yellow semi-solid with 99.47% purity. trace isomer detected |
| 4 | 3 g (1.0 eq.) | 1.20 eq. | DIC (1.00 eq.) | OxymaPure ® (1.00 eq) + 2,4,6-collidine (1.3 eq.) | DCM (25 V) | 20-25 | overnight | IPC (3.48% SM3 left, P: 89.8%)8.9 g crude yellow oil obtained |
| 5 | 3 g (1.0 eq.) | 1.20 eq. | EDC•HCl (1.00 eq.) | OxymaPure ® (1.00 eq) + 2,4,6-collidine (1.3 eq.) | DCM (25 V) | 20-25 | overnight | IPC (22.2% SM3 left, P: 73.6%) 9.5 g crude yellow oil obtained |
| 6 | 20.0 g (1.0 eq.) | 1.20 eq. | DIC (1.00 eq.) | OxymaPure ® (1.00 eq) + 2,4,6-collidine (1.3 eq.) | DCM (25V) | 20-25 | overnight | IPC (2.47% SM3 left, P: 94.9%) 29.8 g yellow sticky oil with 98.4% HPLC purity obtained after purification by column |

TABLE 6.1-continued

| | Starting Materials | | | | | Reaction Conditions | | |
|---|---|---|---|---|---|---|---|---|
| Entry | SM3 | Cmpd A3 | Activator | Base/additive | Solv. | Temp (° C.) | Time (h) | Result |
| 7 | 20.0 g (1.0 eq.) | 1.20 eq. | EDC•HCl (1.00 eq.+ 0.3 eq. + 0.1 eq.) | OxymaPure ® (1.00 eq) + 2,4,6-collidine (2.5 eq.) | DCM (25V) | 20-25 | over-night | IPC (2.83% SM3 left, P: 83.1%) |
| 8 | 130.0 g(1.0 eq.) | 1.20 eq. | EDC•HCl (1.0 eq.) | OxymaPure ® (1.00 eq)+ 2,4,6-collidine (1.3 eq.) | DCM (25V) | 20-25 | 14 h | 8.6% SM3 left, P: 85.51% Diastereoisomer: P = 1.04%: 98.95% |

TABLE 7

| | Starting Materials | | | Reaction Conditions | | |
|---|---|---|---|---|---|---|
| Entry | Compound A6 | TFA | solvent | Temp (° C.) | Time (h) | Result |
| 1 | 20 g (1.0 eq.) | 2 V | DCM (10 V) | 15-25 | 21 | 7.6 g brown solid with 90% HPLC purity obtained |
| 2 | 12.3 g (1.0 eq.) | 2 V | DCM (10 V) | 15-25 | 7 | 5.1 g light brown solid, HPLC purity: 9 5.6% |
| 3 | 50 g (1.0 eq.) | 2 V + 0.2 V | DCM (10 V) | 15-25 | 5 | 0.82% compound A6 left, P: 87.9%; 30.2 g light brown solid obtained with 95.0% HPLC purity purification via slurry from ACN |
| 4 | 220 g (1.0 eq.) | 2.2 V | DCM (10 V) | 15-25 | 5 | 0.64% compound3 left, P: 85.2%; 155.2 g light brown solid obtained with 96.1% HPLC purity purification via slurry from MTBE |

TABLE 8.1

| Stage 1 | | | | | | |
|---|---|---|---|---|---|---|
| | Starting Materials 1 | | | Reaction Conditions 1 | | |
| | | | | Temp | Time | Result |
| Entry | Compound A7 | ClCO₂Et | TEA | Solv. | (° C.) | (h) | (HPLC) |
| 1 | 100 mg (1.0 eq.) Purity >98% | 1.05 eq. | 1.05 eq. | THF (20 V) | −25 | 2 | Not very well, Prolong time no progress |

| Stage 2 | | | | |
|---|---|---|---|---|
| Starting Materials 2 | | Reaction Conditions 2 | | |
| TMSCHN₂ (2M in hexane) | n-BuLi (2.5M in hexane) | Temp (° C.) | Time (h) | Result (HPLC) |
| 1.3 eq. | 1.0 eq. | −90 | 5 min | No INT left, trace product detected, MS of main peak: 400 |
| 1.3 eq. | 1.0 eq. | −90 | 5 min | The above peak(MS: 400) disappeared,a lot of compound 7 appeared, |
| 1.3 eq. | 1.0 eq. | −90 | 5 min | the main peak MS: 247 |
| 1.3 eq. | 1.0 eq. | −90 | 5 min | More complex |

TABLE 8.2

| | Stage 1 | | | | | | |
|---|---|---|---|---|---|---|---|
| | Starting Materials 1 | | | | Reaction Conditions 1 | | |
| | | | | | Temp | Time | Results |
| Entry | Compound A7 | (COCl)$_2$ | DMF | solvent | (° C.) | (h) | (HPLC) |
| 1 | 100 mg (1.0 eq.) Purity > 98% | 1.50 eq. | 0.3 eq. | DCM (20 V) | 0-20 | 1 | A lot of compound A7 left., the peak with MS: 400 has appeared |
| | | | | | | 4 | Less compound 8 was left, mainly compound 7 and the peak(MS: 400) were detected |

| | Stage 2 | | | | |
|---|---|---|---|---|---|
| | Starting Materials 2 | | Reaction Conditions 2 | | |
| | TMSCHN$_2$ (2 M in hexane) | n-BuLi (2.5 M in hexane) | Temp (° C.) | Time (h) | Results (HPLC) |
| | N/A | N/A | N/A | N/A | N/A |

TABLE 8.3

| | Stage 1 | | | | | | |
|---|---|---|---|---|---|---|---|
| | Starting Materials 1 | | | | Reaction Conditions 1 | | |
| | | | | | Temp | Time | Results |
| Entry | Compound A7 | CLCO$_2$Et | TEA | solvent | (° C.) | (h) | (HPLC) |
| 1 | 100 mg (1.0 eq.) Purity >98% | 1.05 eq. + 0.3 eq. + 0.3 eq. + 0.3 eq. | 1.05 eq. + 0.3 eq. + 0.3 eq. + 0.3 eq. | DCM (30 V) | 0-25 | overnight | Reaction did not go well, washed with water and brine, concentrated and used directly to the next step |

| Stage 2 | | | | |
|---|---|---|---|---|
| Starting Materials 2 | | Reaction Conditions 2 | | |
| TMSCHN$_2$ (2M in hexane) | n-BuLi (2.5M in hexane) | Temp (° C.) | Time (h) | Results (HPLC) |
| 1.3 eq. | 1.0 eq. | −90 | 30 min | No product |
| 1.3 eq. | 1.0 eq. | −90 | 30 min | No product |
| 1.3 eq. | 1.0 eq. | −90 | 30 min | No product |
| 1.3 eq. | 1.0 eq. | −90 | 30 min | No product |

TABLE 8.4

| | Stage 1 | | | | | | | |
|---|---|---|---|---|---|---|---|---|
| | Starting Materials 1 | | | | | Reaction Conditions 1 | | |
| | | | | | | Temp | Time | Results |
| Entry | Compound A7 | HOBt | EDC. HCL | TEA | Benzotriazole | Solvent | (° C.) | (h) | (HPLC) |
| 1 | 200 mg (1.0 eq.) HPLC Purity >98% | 1.5 eq. | 1.5 eq. | 1.5 eq. | 1.05 eq. + 0.05 eq. | DCM (25 V) | 0-20 | 5 | Acceptable Washed with water and brine, concentrated and used directly to the next step |

TABLE 8.4-continued

| Stage 2 | | | | | |
|---|---|---|---|---|---|
| Starting Materials2 | | | Reaction Conditions2 | | |
| TMSCHN$_2$ (2M in hexane) | n-BuLi (2.5M in hexane) | Solvent | Temp (° C.) | Time (h) | Results (HPLC) |
| 8.0 eq. | 6.0 eq. | THF (25 V) | −90 | 5 min | Adding ~1.0 eq. of lithio-derivatives: trace product detected, main peak MS: 400 Adding additional ~1.0 eq. of lithio-derivatives: no obvious progress Adding additional ~1.0 eq. of lithio-derivatives: work more complex N/A |

TABLE 9

| | Stage 1 | | | | | | Stage 2 | | | |
|---|---|---|---|---|---|---|---|---|---|---|
| | Starting Materials | | | Reaction Conditions | | | Starting Materials | Reaction Conditions | | |
| | | | | Temp | Time | Result | | Temp | Time | Result |
| Entry | Cmpd A7 | ClCOOEt | TEA | (° C.) | (h) | HPLC | CH$_2$N$_2$ in Et$_2$O | ° C. | (h) | HPLC |
| 1 | 210 mg (1.0 eq.) (Cmpd A7: isomer = 95.6%: 2%) | 1.05 eq. | 1.05 eq. | −25 | 2 | 4.4% SM left | 5~10 eq. | 0 ± 5 | 5 | The HPLC showed 69% product and 10% by-product with MS + 1:400 |
| 2 | 3.0 g (1.0 eq.) | 1.05 eq. | 1.05 eq. | −25 | 2 | 4.7% SM left | 5.0 eq. | 0-10 | 14 | 500 mg light yellow solid obtained with 98.9% HPLC purity after purification by column chromatography |
| 3 | 3.0 g (1.0 eq.) | 1.05 eq. | 1.05 eq. | −25 | 2 | 5.9% SM left | 5.0 eq. | 0-10 | 14 | 610 mg yellow solid obtained with 99.2% HPLC purity after purification by column chromatography |

It is to be understood that the foregoing described embodiments and exemplifications are not intended to be limiting in any respect to the scope of the disclosure, and that the claims presented herein are intended to encompass all embodiments and exemplifications whether or not explicitly presented herein All patents and publications cited herein are fully incorporated by reference in their entirety.

What is claimed is:

1. A method of preparing a compound of Formula I:

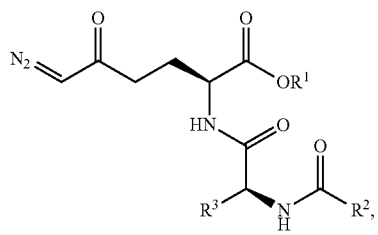

the method comprising:
(a) reacting a compound of Formula II:

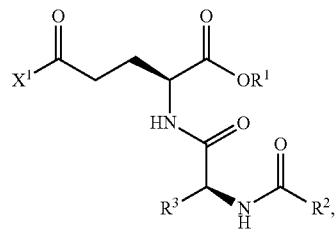

with diazomethane in a solvent at a temperature of about −78° C. to about 0° C., wherein:
$X^1$ is selected from the group consisting of halogen, benzotriazole,

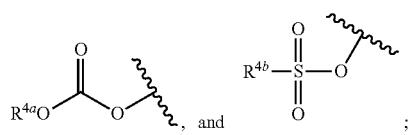

$R^1$ is $C_1$-$C_4$ alkyl;
$R^2$ is $C_1$-$C_4$ alkyl;
$R^3$ is selected from the group consisting of $C_1$-$C_6$ alkyl, (aryl)alkyl, and (heteroaryl)alkyl;
$R^{4a}$ is selected from the group consisting of $C_1$-$C_8$ alkyl and $C_3$-$C_8$ cycloalkyl; and
$R^{4b}$ is selected from the group consisting of $C_1$-$C_8$ alkyl and —$CF_3$.

2. The method of claim 1, wherein:
$X^1$ is:

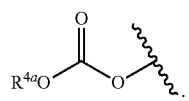

3. The method of claim 2, wherein $R^{4a}$ is ethyl.
4. The method of claim 1, wherein the compound of Formula II is prepared in situ and reacted with diazomethane without isolation or purification.
5. The method of claim 1, wherein the compound of Formula II:

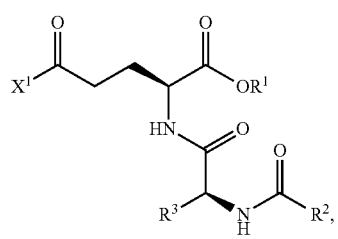

wherein:
$X^1$ is:

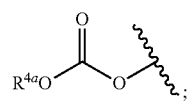

and
$R^{4a}$ is selected from the group consisting of $C_1$-$C_8$ alkyl and $C_3$-$C_8$ cycloalkyl;
is obtained by reacting a compound of Formula III:

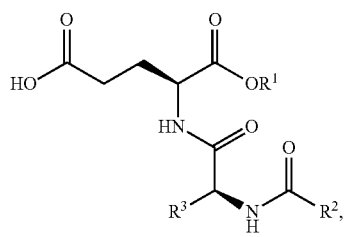

wherein:
$R^1$ is $C_1$-$C_4$ alkyl;
$R^2$ is $C_1$-$C_4$ alkyl; and
$R^3$ is selected from the group consisting of $C_1$-$C_6$ alkyl, (aryl)alkyl, and (heteroaryl)alkyl;
with a compound having Formula IV:

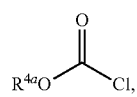

wherein:
$R^{4a}$ is selected from the group consisting of $C_1$-$C_8$ alkyl and $C_3$-$C_8$ cycloalkyl,
in a solvent in the presence of a base at a temperature of about −45° C. to about 20° C.

6. The method of claim 5, wherein the compound of Formula III is obtained by reacting a compound of Formula V:

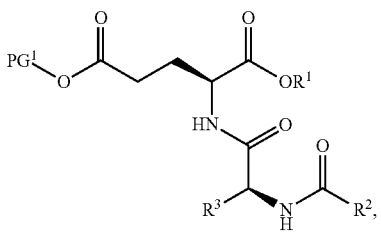

wherein:
R¹ is $C_1$-$C_4$ alkyl;
R² is $C_1$-$C_4$ alkyl;
R³ is selected from the group consisting of $C_1$-$C_6$ alkyl, (aryl)alkyl, and (heteroaryl)alkyl; and
$PG^1$ is a protecting group,
with a deprotecting agent in a solvent at a temperature of about 0° C. to about 60° C.

7. The method of claim 6, wherein $PG^1$ is aralkyl, and the deprotecting agent is hydrogen in the presence of a catalyst.

8. The method of claim 6, wherein the compound of Formula V is obtained by reacting a compound of Formula VI:

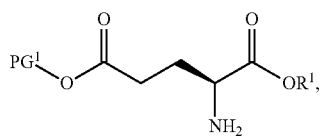

wherein:
R¹ is $C_1$-$C_4$ alkyl; and
$PG^1$ is a protecting group,
with a compound of Formula VII:

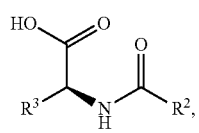

wherein:
R² is $C_1$-$C_4$ alkyl; and
R³ is selected from the group consisting of $C_1$-$C_6$ alkyl, (aryl)alkyl, and (heteroaryl)alkyl;
in a solvent in the presence of a coupling agent at a temperature of about 0° C. to about 60° C.

9. The method of claim 8, wherein the coupling agent comprises dicyclohexylcarbodiimide, diisopropylcarbodiimide, and N-(3-dimethylaminopropyl)-N'-ethylcarbodiimide-HCl.

10. The method of claim 9, wherein the coupling agent further comprises ethyl cyano(hydroxyimino)acetate.

11. The method of claim 8, wherein the compound of Formula VI is obtained by reacting a compound of Formula VIII:

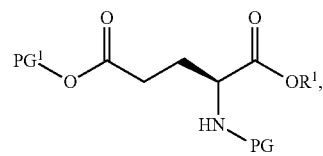

wherein:
R¹ is $C_1$-$C_4$ alkyl;
$PG^1$ is a protecting group; and
PG is a protecting group,
with an amine deprotecting agent in a solvent at a temperature of about 0° C. to about 60° C.,
wherein the amine deprotecting agent selectively removes PG in the presence of $PG^1$.

12. The method of claim 11, wherein PG is selected from the group consisting of fluorenylmethyloxycarbonyl, tert-butyloxycarbonyl, and carboxybenzyl.

13. The method of claim 11 further comprising reacting the

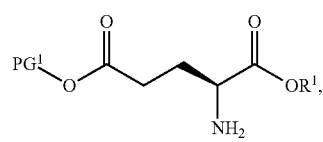

with an acid in a solvent to form a salt that precipitates from solution.

14. The method of claim 11 wherein the compound of Formula VIII is obtained by reacting a compound of Formula IX:

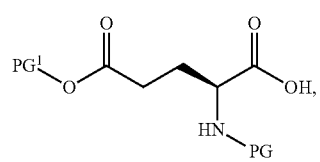

with R¹—X², wherein:
R¹ is $C_1$-$C_4$ alkyl; and
X² is selected from the group consisting of —OH and —Br,
in solvent.

15. The method of claim 1, wherein R¹ is isopropyl.
16. The method of claim 1, wherein R² is methyl.
17. The method of claim 1, wherein R³ is:

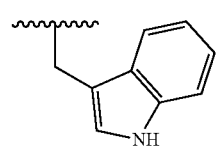

18. The method of claim 1, wherein isopropyl (S)-2-((S)-2-acetamido-3-(1H-indol-3-yl)propanamido)-6-diazo-5-oxohexanoate is obtained in about 10-90% yield starting from a compound of Formula IX.

19. The method of claim 1, wherein isopropyl (S)-2-((S)-2-acetamido-3-(1H-indol-3-yl)propanamido)-6-diazo-5-oxohexanoate is obtained in about 98% chemical purity or more starting from a compound of Formula IX.

20. The method of claim 1, wherein isopropyl (S)-2-((S)-2-acetamido-3-(1H-indol-3-yl)propanamido)-6-diazo-5-oxohexanoate is obtained in about 98% ee or more starting from a compound of Formula IX.

* * * * *

UNITED STATES PATENT AND TRADEMARK OFFICE
CERTIFICATE OF CORRECTION

| | | |
|---|---|---|
| PATENT NO. | : 12,240,797 B2 | Page 1 of 1 |
| APPLICATION NO. | : 17/430286 | |
| DATED | : March 4, 2025 | |
| INVENTOR(S) | : John Philip Lawson | |

It is certified that error appears in the above-identified patent and that said Letters Patent is hereby corrected as shown below:

On the Title Page

Item (71), Lines 2-11, please delete "; Pavel Majer, Sykesville, MD (US); Ivan Sňajdr, Prague (CZ); Martin Hadzima, Kosice (SK); Lukáš Tenora, Kretín (CZ); Jon Philip Lawson, Wildwood, MO (US); Robert Christian Wild, Murrieta, CA (US); Yiyang Shao, Beijing (CN); Jinxiao Chu, Beijing (CN); Jinchao Weng, Beijing (CN)".

Signed and Sealed this
Eighth Day of July, 2025

Coke Morgan Stewart
*Acting Director of the United States Patent and Trademark Office*